(12) United States Patent
Rupprechter et al.

(10) Patent No.: US 9,598,718 B2
(45) Date of Patent: *Mar. 21, 2017

(54) QUANTIFICATION OF MISFOLDED TNFR2:FC

(71) Applicant: Sandoz AG, Basel (CH)

(72) Inventors: Alfred Rupprechter, Kundl (AT); Michael Fuchs, Kundl (AT); Johann Holzmann, Kundl (AT); William Lamanna, Kundl (AT); Christoph Posch, Kundl (AT); Hansjorg Toll, Kundl (AT); Robert Mayer, Kundl (AT)

(73) Assignee: Sandoz AG, Basel (CH)

( * ) Notice: Subject to any disclaimer, the term of this patent is extended or adjusted under 35 U.S.C. 154(b) by 176 days.

This patent is subject to a terminal disclaimer.

(21) Appl. No.: 14/455,183

(22) Filed: Aug. 8, 2014

(65) Prior Publication Data

US 2016/0017403 A1    Jan. 21, 2016

(30) Foreign Application Priority Data

Jul. 18, 2014   (EP) .................................... 14177696

(51) Int. Cl.
*G01N 21/33*   (2006.01)
*C12Q 1/37*    (2006.01)
*G01N 33/68*   (2006.01)
*C07K 14/715*  (2006.01)

(52) U.S. Cl.
CPC ............ *C12Q 1/37* (2013.01); *C07K 14/7151* (2013.01); *G01N 21/33* (2013.01); *G01N 33/6863* (2013.01); *C07K 2319/30* (2013.01); *G01N 2333/70578* (2013.01); *G01N 2440/20* (2013.01)

(58) Field of Classification Search
None
See application file for complete search history.

(56) References Cited

U.S. PATENT DOCUMENTS

| 6,048,728 | A | 4/2000 | Inlow et al. | |
| 7,276,477 | B2 | 10/2007 | Osslund et al. | |
| 7,294,481 | B1 | 11/2007 | Fung | |
| 2011/0151494 | A1* | 6/2011 | Koomen et al. | 435/23 |
| 2014/0065651 | A1* | 3/2014 | Bouvier et al. | 435/23 |
| 2014/0072560 | A1 | 3/2014 | Arakawa et al. | |

FOREIGN PATENT DOCUMENTS

| WO | WO 2011/134920 | 11/2011 |
| WO | WO 2011/134921 | 11/2011 |
| WO | WO 2014/144911 | 9/2014 |

OTHER PUBLICATIONS

Mukai et al., Solution of the structure of the TNF-TNFR2 complex. Sci Signal. Nov. 16, 2010;3(148):ra83. doi: 10.1126/scisignal. 2000954.
Martinez et al., Comparability of a Three-Dimensional Structure in Biopharmaceuticals Using Spectroscopic Methods. J Anal Chem. 2014;2014:1-11.
Goffe et al., Etanercept: an overview. J Am Acad Dermatol. Aug. 2003:S105-11.
U.S. Appl. No. 14/516,992, filed Oct. 17, 2014, Pending.

* cited by examiner

*Primary Examiner* — Michael Borin
(74) *Attorney, Agent, or Firm* — Wolf, Greenfield & Sacks, P.C.

(57) ABSTRACT

The present invention is directed to methods for determining the relative amount of wrongly disulphide bridged TNFR2:Fc in a sample of TNFR2:Fc, a fusion protein which is used in a variety of therapeutic applications. In addition, the invention pertains to a method for purifying TNFR2:Fc using said method for determining the percentage of wrongly disulphide bridged TNFR2:Fc, and to TNFR2:Fc compositions obtained thereby.

20 Claims, 5 Drawing Sheets

T7 (incorrect disulfide bridge Cys$_{78}$-Cys$_{88}$)

T27 (reference peptide)

QUANTIFICATION OF MISFOLDED TNFR2:FC

The present invention is directed to methods for determining the relative amount of a specific wrongly disulphide bridged TNFR2:Fc in a sample of TNFR2:Fc, a fusion protein which is used in a variety of therapeutic applications. In addition, the invention pertains to a method for purifying TNFR2:Fc using said method for determining the relative amount of said specific wrongly disulphide bridged TNFR2:Fc, and to TNFR2:Fc compositions obtained thereby.

RELATED APPLICATIONS

This application claims priority to European Patent Application No. 14177696.3, filed on Jul. 18, 2014, the content of which is herein incorporated by reference in the entirety.

BACKGROUND OF THE INVENTION

Tumor Necrosis Factor alpha (TNF-alpha) is a member of a group of cytokines that stimulate the acute phase reaction, and thus is a cytokine involved in systemic inflammation. TNF-alpha is able to induce inflammation, induce apoptotic cell death, and to inhibit tumorgenesis and viral replication. Dysregulation of TNF-alpha production has been implicated in a variety of human diseases like autoimmune disease, ankylosing spondylitis, juvenile rheumatoid arthritis, psoriasis, psoriatic arthritis, rheumatoid arthritis, Wegener's disease (granulomatosis), Crohn's disease or inflammatory bowel disease, chronic obstructive pulmonary disease (COPD), Hepatitis C, endometriosis, asthma, cachexia, atopic dermatitis, Alzheimer as well as cancer.

Its receptor molecules include TNFR1 and TNFR2. TNF-R1 is expressed in most tissues, whereas TNF-R2 is found only in cells of the immune system. Upon contact with TNF-alpha homotrimers, TNF receptors form trimers and thereby initiate intracellular cell signaling.

Accordingly, soluble TNFR molecules or fragments thereof, which are able to bind to TNF-alpha, can be used as a competitive inhibitor for TNF-alpha. The present disclosure relates to such soluble TNFR2 molecules fused to an Fc portion of a human immunoglobulin (TNFR2:Fc), and more particularly to methods for determining, obtaining and purifying such TNFR2:Fc molecules.

TNFR2:Fc can be manufactured by a bioprocess using recombinant CHO cells, e.g. using dihydrofolate reductase deficient (dhfr-) CHO cells. One particular form of TNFR2:Fc is etanercept which consists of 934 amino acids with an apparent molecular weight of 125 kDa. It comprises a homodimer of the extracellular ligand-binding portion of human tumor necrosis factor receptor (p75) linked to the Fc portion of a human IgG1. The Fc component in both molecules of the homodimer contains the complete hinge, CH2 and CH3 regions, but not the CH1 region of IgG1 (cf. FIG. 1). It is preferably synthesized as a dimeric, secreted, soluble protein while dimerization of the Fc region via three disulphide bonds occurs post-translationally.

By use of X-ray crystallography as well as of mass spectrometry, the complete disulphide bridging pattern of a preferred form of human TNFR2:Fc, etanercept, could be elucidated (see Table 1). Relevant parts of the resolved structures of TNFR2 and its interface with TNF-alpha are shown in FIG. 2 and FIG. 3, whereas connectivity of disulphide variants for the main TNFR2:Fc variant is summarized in Table 1 (see also FIG. 4).

TABLE 1

Disulphide bridging pattern of etanercept

| Intra-chain (Receptor/Fc-part) | | Inter-chain |
| --- | --- | --- |
| Cys(18)-Cys(31) | Cys(98)-Cys(115) | Cys(240)-Cys(240') |
| Cys(32)-Cys(45) | Cys(121)-Cys(139) | Cys(246)-Cys(246') |
| Cys(35)-Cys(53) | Cys(142)-Cys(157) | Cys(249)-Cys(249') |
| Cys(56)-Cys(71) | Cys(163)-Cys(178) | |
| Cys(74)-Cys(88) | Cys(281)-Cys(341) | |
| Cys(78)-Cys(96) | Cys(387)-Cys(445) | |
| Cys(104)-Cys(112) | | |

However, misfolded TNFR2:Fc has been found in all analysed TNFR2:Fc preparations. Such misfolded TNFR2:Fc is not preferred when TNFR2:Fc is used in any of the above-noted therapies. U.S. Pat. No. 7,294,481 reports that such misfolded TNFR:Fc such as TNFR2:Fc is formed early in the cell culture process, is transported and represents a significant proportion (about 25-50%) of the expression product. It is further reported that such misfolded TNFR:Fc can be reduced, if the TNFR:Fc producing host cell is cultured at a temperature of 25-34° C. during the production phase. Moreover, it is reported that such misfolded TNFR:Fc can be separated by hydrophobic interaction chromatography.

However, as shown in the examples section herein, the currently available TNFR2:Fc preparations (marketed as ENBREL®) still contain wrongly disulphide bridged TNFR2:Fc (see Table 4 below). This may be due to the difficulty of separating same from correctly folded TNFR2:Fc.

Accordingly, there is a need in the art for methods for determining the purity of TNFR2:Fc in a sample—here the amount of wrongly disulphide bridged TNFR2:Fc—which allow for the selection of, e.g., fractions having the desired higher degree of purity.

SUMMARY OF THE INVENTION

The inventors identified a TNFR2:Fc variant comprising a wrongly bridged disulphide in the binding region of the TNF-alpha receptor part to TNF-alpha ($Cys_{78}$-$Cys_{88}$) (cf. FIGS. 5 and 6). It is demonstrated herein by correlations between the bioactivity and the amount of wrongly bridged variant $Cys_{78}$-$Cys_{88}$ ("T7 variant" or "T7"), that high amounts of this variant T7 have a negative impact on potency (cf. FIG. 7).

Starting from this finding, the inventors developed a method for quantitation of T7 variant by non-reducing peptide mapping. By digesting TNFR2:Fc samples with trypsin under non-reducing conditions, the protein can be cleaved into smaller components, while the disulphide bridge structures remain intact. Afterwards, the yielded peptides are further chromatographically separated by reversed phase chromatography and detected via UV/Vis detection. This method allows for relative quantification of the amount of the so-called T7 peptide which is a peptide obtained from incorrectly bridged T7 variants. Preferably, the amount of incorrectly bridged T7 peptide can be determined from the signal for the T7 peptide in the obtained chromatogram. E.g. it can be expressed as the peak area for the T7 peptide relative to the peak area for a reference peptide, which is not affected by disulphide bridging or a reference peptide which is not affected by the disulphide bridging of the residues $Cys_{74}$, $Cys_{78}$, $Cys_{88}$ and $Cys_{96}$. By use of the newly developed method it is possible to identify samples in which correctly disulphide bridged TNFR2:Fc and T7 variant co-elute, and which may therefore not be pooled with pure TNFR2:Fc samples and/or samples with a reduced amount of T7 variant, thereby achieving an improved purity/potency of the final TNFR2:Fc composition.

More specifically, provided is a method for determining $Cys_{78}$-$Cys_{88}$ disulphide bridged TNFR2:Fc (i.e. T7 variant) in a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc, wherein the method comprises the steps of:
(a) providing a sample comprising a mixture of $Cys_{78}$-$Cys_{88}$ disulphide bridged TNFR2:Fc and $Cys_{74}$-$Cys_{88}$/$Cys_{78}$-$Cys_{96}$ disulphide bridged TNFR2:Fc;
(b) denaturing and alkylating the sample of step (a);
(c) subjecting the sample resulting from step (b) to tryptic digestion;
(d) subjecting the sample resulting from step (c) to HPLC, thereby separating fragments indicative of $Cys_{78}$-$Cys_{88}$ disulphide bridged TNFR2:Fc; and
(e) conducting a peak integration for the peak indicative of $Cys_{78}$-$Cys_{88}$ disulphide bridged TNFR2:Fc and for a peak not affected by disulphide bridging of $Cys_{74}$, $Cys_{78}$, $Cys_{88}$ and $Cys_{96}$, as obtained from step (d);
wherein the amino acid sequence of the TNFR2 part of TNFR2:Fc has at least 97%, preferably at least 98%, more preferably at least 99% identity; most preferably 100% identity to the amino acids 23-257 of the amino acid sequence of SEQ ID NO: 1.

Also provided is a method of purifying $Cys_{74}$-$Cys_{88}$/$Cys_{78}$-$Cys_{96}$ disulphide bridged TNFR2:Fc, wherein the method comprises subjecting a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc to at least one chromatographic step, wherein the at least one chromatographic step comprises a hydrophobic interaction chromatography (HIC); and separating one or more fractions comprising $Cys_{74}$-$Cys_{88}$/$Cys_{78}$-$Cys_{96}$ disulphide bridged TNFR2:Fc which have a reduced amount of $Cys_{78}$-$Cys_{88}$ disulphide bridged TNFR2:Fc as compared to the sample subjected to said at least one chromatographic step; wherein said one or more fractions comprise less than 2.2% $Cys_{78}$-$Cys_{88}$ disulphide bridged TNFR2:Fc on the basis of total TNFR2:Fc, preferably less than 2.1%, preferably less than 2.0%, preferably less than 1.9%, preferably less than 1.8%, more preferably less than 1.7%, even more preferably less than 1.6%, and most preferably 1.5% or less $Cys_{78}$-$Cys_{88}$ disulphide bridged TNFR2:Fc, when determined using the method for determining $Cys_{78}$-$Cys_{88}$ disulphide bridged TNFR2:Fc in a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc disclosed herein and using peak integration of T7 (SEQ ID NO: 4) and T27 (SEQ ID NO: 5) peptide signals and calculating the relative amount by formula (1) as described below.

Further provided is a method of purifying $Cys_{74}$-$Cys_{88}$/$Cys_{78}$-$Cys_{96}$ disulphide bridged TNFR2:Fc, wherein the method comprises subjecting a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc to at least one chromatographic step, wherein the at least one chromatographic step comprises a hydrophobic interaction chromatography (HIC); and separating one or more fractions comprising $Cys_{74}$-$Cys_{88}$/$Cys_{78}$-$Cys_{96}$ disulphide bridged TNFR2:Fc which have a reduced amount of $Cys_{78}$-$Cys_{88}$ disulphide bridged TNFR2:Fc as compared to the sample subjected to said at least one chromatographic step; wherein the amount of $Cys_{78}$-$Cys_{88}$ disulphide bridged TNFR2:Fc is determined using a method as disclosed herein.

In addition, the present disclosure provides a method comprising
(a) producing a composition comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc in a suitable host cell; and
(b) purifying the obtained combination of $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc by the purification method as disclosed herein.

Finally, also disclosed is a composition of TNFR2:Fc, wherein the amino acid sequence of the TNFR2:Fc has at least 97%, preferably at least 98%, more preferably at least 99% identity; most preferably 100% to the amino acid sequence of SEQ ID NO: 3, comprising less than 2.2% $Cys_{78}$-$Cys_{88}$ disulphide bridged TNFR2:Fc, preferably less than 2.1%, preferably less than 2.0%, preferably less than 1.9%, preferably less than 1.8%, more preferably less than 1.7%, even more preferably less than 1.6%, and most preferably 1.5% or less $Cys_{78}$-$Cys_{88}$ disulphide bridged TNFR2:Fc, when determined using the method for determining $Cys_{78}$-$Cys_{88}$ disulphide bridged TNFR2:Fc in a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc disclosed herein and using peak integration of T7 (SEQ ID NO: 4) and T27 (SEQ ID NO: 5) peptide signals and calculating the relative amount by formula (1) as described below.

Such a composition is particularly suitable for use in medicine, e.g. for use in the prevention and/or treatment of a disease selected from autoimmune disease, ankylosing spondylitis, juvenile rheumatoid arthritis, psoriasis, psoriatic arthritis, rheumatoid arthritis, granulomatosis, inflammatory bowel disease, chronic obstructive pulmonary disease (COPD), Hepatitis C, endometriosis, asthma, cachexia, atopic dermatitis, Alzheimer, and cancer; preferably in the treatment of a disease selected from ankylosing spondylitis, juvenile rheumatoid arthritis, psoriasis, psoriatic arthritis and rheumatoid arthritis.

DETAILED DESCRIPTION OF THE PREFERRED EMBODIMENTS

The present disclosure provides a method for determining $Cys_{78}$-$Cys_{88}$ disulphide bridged TNFR2:Fc in a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc, wherein the method comprises the steps of:
(a) providing a sample comprising a mixture of $Cys_{78}$-$Cys_{88}$ disulphide bridged TNFR2:Fc and $Cys_{74}$-$Cys_{88}$/$Cys_{78}$-$Cys_{96}$ disulphide bridged TNFR2:Fc;
(b) denaturing and alkylating the sample of step (a);
(c) subjecting the sample resulting from step (b) to tryptic digestion;
(d) subjecting the sample resulting from step (c) to HPLC, thereby separating fragments indicative of $Cys_{78}$-$Cys_{88}$ disulphide bridged TNFR2:Fc; and
(e) conducting a peak integration for the peak indicative of $Cys_{78}$-$Cys_{88}$ disulphide bridged TNFR2:Fc and for a peak not affected by disulphide bridging of $Cys_{74}$, $Cys_{78}$, $Cys_{88}$ and $Cys_{96}$, as obtained from step (d);
wherein the amino acid sequence of the TNFR2 part of TNFR2:Fc has at least 97%, preferably at least 98%, more preferably at least 99% identity; most preferably 100% identity to the amino acids 23-257 of the amino acid sequence of SEQ ID NO: 1. Amino acids 1-22 of SEQ ID NO: 1 correspond to the signal peptide clipped off in the mature secreted protein.

In the context of the present disclosure, the TNFR2 part of TNFR2:Fc refers to any TNFR polypeptide having at least 97%, preferably at least 98%, more preferably at least 99%, and most preferably 100% identity over the full length of an amino acid sequence comprising at least 150-235, preferably 200-235, and most preferably 233-235 amino acids of the extracellular part of TNFR2, and still binding to TNF-alpha, as determined by ELISA or any other convenient assay. More preferably, said TNFR is capable of binding to TNF-alpha and Lymphotoxin alpha (LT-alpha), as determined by ELISA or any other convenient assay. Such assays are well-known to the skilled person.

The CDS and protein sequences of TNFR2 (TNF receptor type 2; CD120b; p75/80; for human: RefSeq (mRNA): NM_001066, RefSeq (protein): NP_001057 (SEQ ID NO:1)) are known in the art.

Generally, a polypeptide has "at least x % identity" over the full length of a defined length of amino acids with another polypeptide if the sequence in question is aligned with the best matching sequence of the amino acid sequence and the sequence identity between those to aligned sequences is at least x %. Such an alignment can be performed using for example publicly available computer homology programs such as the "BLAST" program, such as "blastp" provided at the NCBI homepage at www.ncbi.nlm.nih.gov/blast/blast.cgi, using the default settings provided therein. Further methods of calculating sequence identity percentages of sets of polypeptides are known in the art.

The Fc-region (fragment crystallisable region) refers to the tail region of an antibody, in the case of IgG composed of the second and third constant domain of the antibody's two heavy chains. In certain embodiments, the Fc polypeptide comprises the constant region of an IgG class heavy chain or a fragment and/or variant thereof and in other embodiments the constant region of other immunoglobulin isotypes can be used to generate such TNFR2:Fc fusions. For example, a TNFR2:Fc polypeptide comprising the constant region of an IgM class heavy chain or a fragment and/or variant thereof could be used. Preferably, the Fc fragment is derived from IgG, more preferably from IgG1, even more preferably from human IgG1. The constant region of immunoglobulin heavy chains, with a specific example of a human IgG1 class heavy chain constant domain provided by SEQ ID NO: 2, comprises a CH1 domain (amino acids 1 through 98 of SEQ ID NO: 2), a hinge region (amino acids 99 through 110 of SEQ ID NO:2), a CH2 domain (amino acids 111 through 223 of SEQ ID NO:2), and a CH3 domain (amino acids 224 through 330 of SEQ ID NO: 2). As used herein, an Fc domain can contain one or all of the heavy chain CH1 domain, hinge region, CH2, and CH3 domains described above, or fragments or variants thereof. Certain embodiments of the invention include TNFR2:Fc comprising all or a portion of the extracellular domain of TNFR2 (SEQ ID NO:1) fused to all or a portion of SEQ ID NO: 2, optionally with a linker polypeptide between the TNFR2 portion and the Fc portion of the TNFR2:Fc. For example, CH1, CH2 and the entire hinge region may be present in the molecule. In further embodiments, a heavy chain constant region comprising at least a portion of CH1 is the Fc portion of a TNFR2:Fc. Certain embodiments can also include, for example, all of the hinge region or the C-terminal half of the hinge region to provide a disulphide bridge between heavy chains. If a multimeric, e.g. a dimeric TNFR2:Fc is desired, it is important to include the portion of the hinge region implicated in disulphide bond formation between the heavy chains (for example, a portion of amino acids 99 through 110 of SEQ ID NO: 2 that includes amino acid 109 of SEQ ID NO: 2). In a preferred embodiment, the Fc portion consists of the full hinge region and the CH2 and CH3 domains. However, the TNFR2:Fc can comprise portions of the CH3 domain that do not include the C-terminal lysine residue (amino acid 330 of SEQ ID NO: 2), as this residue has been observed to be removed in post-translational processing of IgG heavy chain polypeptides. Fc fusions and Fc fragments are well-known in the art. Preferably, the TNFR2:Fc is essentially identical/similar to etanercept, more preferably, the TNFR2:Fc is etanercept. Etanercept is a dimer of two molecules of the extracellular portion of the p75 TNF-alpha receptor, each molecule consisting of a 235 amino acid TNFR-derived polypeptide that is fused to a 232 amino acid Fc portion of human IgG1. The amino acid sequence of the monomeric component of etanercept is shown as SEQ ID NO: 3. In the dimeric form of this molecule, two of these fusion polypeptides (or "monomers") are held together by three disulphide bonds that form between the immunoglobulin portions of the two monomers. The etanercept dimer therefore consists of 934 amino acids, and has an apparent molecular weight of approximately 125 kilodaltons. In North America, etanercept is marketed by Amgen under the trade name Enbrel®. Wyeth/Pfizer is the sole marketer of Enbrel® outside of North America excluding Japan where Takeda Pharmaceuticals markets the drug.

The term "essentially identical/similar to etanercept" as used herein means that the amino acid sequence of the TNFR2:Fc applied to step (a) has at least 97% identity to the amino acid sequence shown in SEQ ID NO: 3, preferably at least 98% identity, more preferably 99% identity to the amino acid sequence shown in SEQ ID NO: 3. Alternatively or additionally, the TNFR2:Fc may have 100% sequence identity to the amino acid sequence of SEQ ID NO: 3, and may or may not differ from etanercept by posttranslational modifications (only), e.g. by glycosylation. Suitable procedures for changing a glycosylation pattern and tests for determining a glycosylation pattern are well known to the skilled person.

The TNFR2:Fc may be recombinantly produced, preferably by using a mammalian cell based expression system. Preferably, said mammalian cell-based expression system is at least one selected from the group consisting of Baby hamster kidney cell lines (e.g., BHK21); Chinese hamster ovary cell lines (e.g., CHO-K1, CHO-DG44, CHO-DXB, or CHO-dhfr-); Murine myeloma cell lines (e.g., SP2/0); Mouse myeloma cell lines (e.g., NS0); Human embryonic kidney cell lines (e.g., HEK-293); Human-retina-derived cell lines (e.g., PER-C6), and/or Amniocyte cell lines (e.g., CAP). Preferably, hamster cell based expression systems are being used. BHK21 ("Baby Hamster Kidney") cells belong to a quasi-diploid established line of Syrian hamster cells, descended from a clone from an unusually rapidly growing primary culture of newborn hamster kidney tissue. Non limiting examples for BHK-21 cell lines which are commercially available and can be used in the context of the present invention are BHK-21 (C-13); BHK21-pcDNA3.1-HC; BHK570; Flp-In-BHK Cell Line; and/or BHK 21 (Clone 13) hamster cell line.

Chinese hamster ovary (CHO) cells are a cell line derived from the ovary of the Chinese hamster. They are often used in biological and medical research and are commercially utilized in the production of therapeutic proteins. They were introduced in the 1960s and were originally grown as a monolayer culture. Today, CHO cells are the most commonly used mammalian hosts for industrial production of recombinant protein therapeutics and are usually grown in suspension culture.

Non limiting examples for CHO cell lines which are commercially available and can be used in the context of the present invention are FreeStyle CHO-S cells; ER-CHO Cell Line; CHO 1-15 500 CHINESE HAM; CHO-DXB, CHO-dhfr-, CHO DP-12 clone#1934; CHO-CD36; CHO-ICAM-1; CHO-K1; Ovary; HuZP3-CHOLec3.2.8.1; xrs5; CHO-K1/BB2 Cells; CHO-K1/BB3 Cells; CHO-K1/EDG8/Galpha15 Cells; CHO-K1/M5 Cells; CHO-K1/NK1 Cells; CHO-K1/NK3 Cells; CHO-K1/NMUR1 Cells; CHO-K1/NTSR1 Cells; CHO-K1/OX1 Cells; CHO-K1/PAC1/Gα15 Cells; CHO-K1/PTAFR Cells; CHO-K1/TRH1 Cells; CHO-K1/V1B Cells; 5HT1A Galpha-15-NFAT-BLA CHO-K1 Cell Line; AVPR2 CRE-BLA CHO-K1 Cell Line; CHO-S Cells SFM Adapted; DG44 Cells; Flp-In-CHO Cell Line; GeneSwitch-CHO Cell Line; NFAT-bla CHO-K1 Cell Line; T-REx-CHO Cell Line; GenoStat CHO K-1 Stable Cell Line; GenoStat CHO K-1 Stable Cell Line Kit; CHO-K1 Cell Line hamster, CHO-PEPT1 Cell line, CHO SSF3 and/or CHO-HPT1 Cell Line. In a particularly preferred embodiment, the hamster cell-based expression system is a CHO-dhfr-cell line.

The sample comprising the TNFR2:Fc to be applied in step (a) may be a cell culture material, such as a cell culture supernatant or a cell lysate. Preferably the solution is a cell-free and serum-free cell culture supernatant. In an even more preferred embodiment, the solution is further purified, e.g. by affinity chromatography and/or hydrophobic interaction chromatography. Generally the TNFR2:Fc applied in step (a) of the method disclosed herein comprises a mixture of $Cys_{78}$-$Cys_{88}$ disulphide bridged TNFR2:Fc and $Cys_{74}$-$Cys_{88}$/$Cys_{78}$-$Cys_{96}$ disulphide bridged TNFR2:Fc.

In a preferred embodiment, the denaturing and alkylating step (b) is carried out in a buffer having a pH in the range of 7 to 9, preferably 7.5 to 8.5, most preferably about pH 8. For example, the buffer may be a TRIS buffer, such as a buffer comprising 10-100 mM TRIS, more preferably 20-80 mM TRIS. The buffer further comprises an alkylating agent, for example 0.5-1.5M iodoacetamide, preferably 0.9-1.2M iodoacetamide. It is further preferred that the buffer of step (b) comprises 0.02%-0.5% of a cleavable surfactant, preferably 0.1%-0.2% of a cleavable surfactant. In general, any cleavable surfactant which does not interfere with tryptic digestion may be used. Particularly preferred cleavable surfactants are selected from sodium 3-[(2-methyl-2-undecyl-1,3-dioxolan-4-yl)-methoxy]-1-propanesulfonate, sodium 3-((1-(furan-2-yl)undecyloxy)carbonylamino)-propane-1-sulfonate, and sodium 3-(4-(1,1-bis(hexyloxy)ethyl)pyridinium-1-yl)propane-1-sulfonate. In a more preferred embodiment, the surfactant is sodium 3-[(2-methyl-2-undecyl-1,3-dioxolan-4-yl)methoxy]-1-propanesulfonate. In general, step (b) is carried out at a temperature and for a time sufficient to denature and alkylate the TNFR2:Fc mixture applied in step (a). For example, step (b) may be carried out at 40 to 70° C. for 30 to 60 min. In a preferred embodiment, step (b) may be carried out at 50 to 60° C. for 30 to 45 min.

The tryptic digest in step (c) is carried out using an effective amount of trypsin and applying a sufficient time and an appropriate temperature under conditions, which facilitate digestion. For example, the tryptic digest may be carried out in a suitable buffer for 1-24 h, preferably for 6-18 h; and at 32-38°, such as at 36-37° C. In many cases the buffer conditions in step (b) will not be suitable for step (c). In these cases, step (c) may comprise exchanging the buffer of the sample obtained from step (b) into a suitable digestion buffer prior to the digest. Preferably, said digestion buffer has a pH in the range of 5 to 7, more preferably in the range of 5.5 to 6.5. Suitable digestion buffers include digestion buffers comprising MES as the buffering agent, e.g. in a concentration of 10-100 mM MES, more preferably 30-60 mM MES. In addition to the buffering agent, the digestion buffer may also comprise a cleavable surfactant. The cleavable surfactant may be the same as used in step (b) or may be a different cleavable surfactant. Accordingly, the cleavable surfactant may be selected from sodium 3-[(2-methyl-2-undecyl-1,3-dioxolan-4-yl)methoxy]-1-propanesulfonate, sodium 3-((1-(furan-2-yl)undecyloxy)carbonylamino)propane-1-sulfonate, and sodium 3-(4-(1,1-bis(hexyloxy)ethyl)pyridinium-1-yl)propane-1-sulfonate. In a more preferred embodiment the surfactant is sodium 3-[(2-methyl-2-undecyl-1,3-dioxolan-4-yl)methoxy]-1-propanesulfonate. If present, the digestion buffers comprises 0.02%-0.5% of a cleavable surfactant, preferably 0.1%-0.2% cleavable surfactant. Finally, step (c) may be terminated by addition of 1% formic acid in 10% acetonitrile. The skilled person will note that this digest is performed under non-reducing conditions.

In Table 2, all the fragments are listed which are obtained in a tryptic digest of a preferred TNFR2:Fc, namely etanercept, under reducing (!) conditions.

TABLE 2

| Peptide No. | No. Amino acid | SEQ ID NO: | Sequence |
| --- | --- | --- | --- |
| T1 | 1-19 | 6 | LPAQVAFTPYAPEPGSTCR |
| T2 | 20-21 |  | LR |
| T3 | 22-34 | 7 | EYYDQTAQMCCSK |
| T4 | 35-42 | 8 | CSPGQHAK |
| T5 | 43-47 | 9 | VFCTK |
| T6 | 48-77 | 10 | TSDTVCDSCEDSTYTQLWNWVPECLSCGSR |
| T7 | 78-90 | 4 | CSSDQVETQACTR |
| T8 | 91-94 | 11 | EQNR |
| T9 | 95-108 | 12 | ICTCRPGWYCALSK |

TABLE 2-continued

| Peptide No. | No. Amino acid | SEQ ID NO: | Sequence |
|---|---|---|---|
| T10 | 109-113 | 13 | QEGCR |
| T11 | 114-119 | 14 | LCAPLR |
| T12 | 120-120 | | K |
| T13 | 121-185 | 15 | CRPGFGVARPGTETSDVVCKPCAPGTFSNTTSS TDICRPHQICNVVAIPGNASMDAVCTSTSPTR |
| T14 | 186-201 | 16 | SMAPGAVHLPQPVSTR |
| T15 | 202-238 | 17 | SQHTQPTPEPSTAPSTSFLLPMGPSPPAEGSTGDEPK |
| T16 | 239-242 | 18 | SCDK |
| T17 | 243-268 | 19 | THTCPPCPAPELLGGPSVFLFPPKPK |
| T18 | 269-275 | 20 | DTLMISR |
| T19 | 276-294 | 21 | TPEVTCVVVDVSHEDPEVK |
| T20 | 295-308 | 22 | FNWYVDGVEVHNAK |
| T21 | 309-312 | 23 | TKPR |
| T22 | 313-321 | 24 | EEQYNSTYR |
| T23 | 322-337 | 25 | VVSVLTVLHQDWLNGK |
| T24 | 338-340 | | EYK |
| T25 | 341-342 | | CK |
| T26 | 343-346 | 26 | VSNK |
| T27 | 347-354 | 5 | ALPAPIEK |
| T28 | 355-358 | 27 | TISK |
| T29 | 359-360 | | AK |
| T30 | 361-364 | 28 | GQPR |
| T31 | 365-375 | 29 | EPQVYTLPPSR |
| T32 | 376-380 | 30 | EEMTK |
| T33 | 381-390 | 31 | NQVSLTCLVK |
| T34 | 391-412 | 32 | GFYPSDIAVEWESNGQPENNYK |
| T35 | 413-429 | 33 | TTPPVLDSDGSFFLYSK |
| T36 | 430-434 | 34 | LTVDK |
| T37 | 435-436 | | SR |
| T38 | 437-459 | 35 | WQQGNVFSCSVMHEALHNHYTQK |
| T39 | 460-467 | 36 | SLSLSPGK |

Taking into consideration the disulphide bridging of etanercept shown in Table 1, skilled person will immediately realize that under non-reducing conditions as provided in the determination method of the present invention, e.g. the individual fragments T1 (aa 1-19) and T3 (aa 22-34) will not be obtained in TNFR2:Fc molecules with an intact $Cys_{18}$-$Cys_{31}$ disulphide bridge as they are still covalently bound by this disulphide bridge. Similarly, fragment T7 (aa 78-90) will not be obtained from TNFR2:Fc molecules with intact $Cys_{74}$-$Cys_{88}$ and/or $Cys_{78}$-$Cys_{96}$ disulphide bridges. However, if $Cys_{78}$ is forming a disulphide bridge with $Cys_{88}$, a fragment corresponding to amino acids 78-90 of TNFR2:Fc will be obtained.

Then, the sample resulting from step (c) is subjected to HPLC, thereby separating the individual fragments obtained in the tryptic digest. In particular, according to the method presented herein, fragments indicative of $Cys_{78}$-$Cys_{88}$ disulphide bridged TNFR2:Fc from the other fragments, in particular from fragments indicative of $Cys_{74}$-$Cys_{88}$ and/or $Cys_{78}$-$Cys_{96}$ disulphide bridged TNFR2:Fc. In a particularly preferred embodiment, the fragments indicative of $Cys_{78}$-$Cys_{88}$ disulphide bridged TNFR2:Fc comprise, preferably consist of the amino acid sequence shown in SEQ ID NO: 4 ("T7", see also above Table 2).

The conditions applied in HPLC may differ dependent on the equipment and conditions used, but a person skilled in the art will be readily enabled to determine same by routine measures and in light of the additional guidance provided in the examples section below. Particular suitable columns for HPLC are those which allow separation of peptide fragments, and using any suitable mobile phase maintaining the non-reducing conditions. In one embodiment, step (d) is carried out in a mobile phase comprising 0.05%-0.5% TFA in water, preferably 0.1%-0.2% TFA in water.

Using the chromatogram obtained in step (d), the skilled person can conduct a peak integration for the peak indicative of $Cys_{78}$-$Cys_{88}$ disulphide bridged TNFR2:Fc. In order to assess the relative amount of $Cys_{78}$-$Cys_{88}$ disulphide bridged TNFR2:Fc it is most suitable to compare the peak area indicative if this TNFR2:Fc isoform with the area of a peak not affected by any disulphide bridging of residues $Cys_{74}$, $Cys_{78}$, $Cys_{88}$ and $Cys_{96}$. Preferably, the peak not affected by disulphide bridging of residues $Cys_{74}$, $Cys_{78}$, $Cys_{88}$ and $Cys_{96}$ is a peak of a fragment which is not affected by disulphide bridging at all and hence, indicative of the total TNFR:Fc in the sample, regardless of the disulphide bridging. Even more preferred, this reference peak is corresponds to a peptide furthermore not affected by glycosylation or any other posttranslational modification. In a particularly preferred embodiment, the fragments indicative of total TNFR2:Fc comprise, preferably consist of the amino acid sequence shown in SEQ ID NO: 5 ("T27", see also above Table 2). However, it will be acknowledged that other fragments which are not affected by disulphide bridging of $Cys_{74}$, $Cys_{78}$, $Cys_{88}$ and $Cys_{96}$ may be used as well, in particular in view of the known disulphide bridging pattern provided in Table 1 above.

In a most preferred embodiment, the fragments indicative of $Cys_{78}$-$Cys_{88}$ disulphide bridged TNFR2:Fc comprise, preferably consist of the amino acid sequence shown in SEQ ID NO: 4 ("T7"); and the fragments indicative of total TNFR2:Fc comprise, preferably consist of the amino acid sequence shown in SEQ ID NO: 5 ("T27"). In this case, the relative amount of $Cys_{78}$-$Cys_{88}$ disulphide bridged TNFR2:Fc is determined by (i) integrating the peak areas in the HPLC chromatogram indicative of $Cys_{78}$-$Cys_{88}$ disulphide bridged TNFR2:Fc ("T7 area") and indicative of total TNFR2:Fc ("T27 area"); and
(ii) calculating the relative amount according to formula (1).

$$rel. \%(T7) = \frac{area(T7)}{area(T7) + area(T27)} \times 100 \quad (1)$$

area(T7): peak area of fragment T7 (SEQ ID NO: 4)
area(T27): peak area of fragment T27 (SEQ ID NO: 5)

The above disclosed method for determining $Cys_{78}$-$Cys_{88}$ disulphide bridged TNFR2:Fc in a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc can be advantageously used in quality management as well as in the purification process of TNFR2:Fc.

Accordingly, also provided is a method of purifying $Cys_{74}$-$Cys_{88}$/$Cys_{78}$-$Cys_{96}$ disulphide bridged TNFR2:Fc, wherein the method comprises
subjecting a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc to at least one chromatographic step, wherein the at least one chromatographic step comprises a hydrophobic interaction chromatography (HIC); and
separating one or more fractions comprising $Cys_{74}$-$Cys_{88}$/$Cys_{78}$-$Cys_{96}$ disulphide bridged TNFR2:Fc which have a reduced amount of $Cys_{78}$-$Cys_{88}$ disulphide bridged TNFR2:Fc as compared to the sample subjected to said at least one chromatographic step;
wherein said one or more fractions comprise less than 2.2% $Cys_{78}$-$Cys_{88}$ disulphide bridged TNFR2:Fc on the basis of total TNFR2:Fc, preferably less than 2.1%, preferably less than 2.0%, preferably less than 1.9%, preferably less than 1.8%, more preferably less than 1.7%, even more preferably less than 1.6%, and most preferably 1.5% or less $Cys_{78}$-$Cys_{88}$ disulphide bridged TNFR2:Fc when determined using the method using peak integration of T7 and T27 and calculating the relative amount by formula (1) as described above.

Likewise, the present disclosure provides a method of purifying $Cys_{74}$-$Cys_{88}$/$Cys_{78}$-$Cys_{96}$ disulphide bridged TNFR2:Fc, wherein the method comprises
subjecting a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc to at least one chromatographic step, wherein the at least one chromatographic step comprises a hydrophobic interaction chromatography (HIC); and
separating one or more fractions comprising $Cys_{74}$-$Cys_{88}$/$Cys_{78}$-$Cys_{96}$ disulphide bridged TNFR2:Fc which have a reduced amount of $Cys_{78}$-$Cys_{88}$ disulphide bridged TNFR2:Fc as compared to the sample subjected to said at least one chromatographic step;
wherein the amount of $Cys_{78}$-$Cys_{88}$ disulphide bridged TNFR2:Fc is determined using a method as disclosed herein.

In a preferred embodiment of these methods, the amino acid sequence of the TNFR2:Fc has at least 97%, preferably at least 98%, more preferably at least 99% identity; most preferably 100% to the amino acid sequence of SEQ ID NO: 3.

The solution comprising the crude TNFR2:Fc is usually subjected to affinity chromatography as a first step. The term "subjecting a solution comprising said TNFR2:Fc to affinity chromatography" as used herein is intended to indicate that the affinity chromatography is specific for the TNFR2:Fc, i.e. essentially only the TNFR2:Fc is first bound to a resin via an interaction that is specific for the TNFR2:Fc, then the resin is usually washed, whereafter the TNFR2:Fc is eluted from the resin by applying suitable conditions. Affinity resins can be eluted by changing salt concentrations, pH, pI, charge and ionic strength in one or more steps or through a gradient to resolve the TNFR2:Fc. The resin is typically a gel matrix, often of agarose, which has been modified in order to provide for specific interaction with TNFR:Fc.

For example, the affinity chromatography may be carried out on a resin modified with Protein A, Protein G, an antibody capable of binding the Fc-part of said TNFR2:Fc, or an antibody directed against the TNFR2-part of said TNFR2:Fc. Preferably said resin is modified with Protein A or Protein G, and more preferably, said resin is modified with Protein A. Protein A is a protein originally found in the cell wall of *Staphylococcus aureus* which binds with high affinity to human IgG1 and IgG2 as well as mouse IgG2a and IgG2b. In addition, Protein A binds with moderate affinity to human IgA, IgE and IgM as well as to mouse IgG3 and IgG1. It does not react with human IgD or IgG3, or murine IgA, IgE and IgM. Alternatively, other Fc-binding bacterial proteins such as Protein G or Protein A/G may be used. Protein G has a binding affinity to human IgG1, IgG2 and IgG4, and to murine IgG2a and IgG2b that is comparable to Protein A. However, Protein G also binds to human IgG3 and rat immunoglobulins, and its binding affinity to murine IgG1 and IgG3 is increased as compared to Protein A. Protein G exhibits no apparent affinity to IgA, IgD, IgE, or IgM. Protein A/G is a recombinant fusion protein of both Protein A and Protein G. The binding of Protein A/G is less pH-dependent than Protein A, it binds to all subclasses of human and mouse IgG, binds to human IgA, IgE, IgM and (to a lesser extent) IgD, but does not bind mouse IgA or IgM. A particular suitable Protein A resin is MabSelect SuRe resin (GE Healthcare). Said resin has a mean particle size of 85 µm, and a loading capacity of 15-22 g/L resin. If the Fc-part of TNFR2:Fc does not react with Protein A, Protein G or Protein A/G, one may use antibodies which are specific for said Fc-part or the TNFR2-part. Suitable antibodies will be apparent to those skilled in the art and are commercially available.

Binding of the TNFR2:Fc to the affinity matrix or resin usually occurs at pH 6-8, preferably at pH 6.5-7.5, and more preferably at about pH 7.0. Hence, it may be necessary to adjust the pH of the solution prior to binding to the affinity resin. In a preferred embodiment, the resin having bound said TNFR2:Fc is then washed with one or more suitable buffers. Such buffers can comprise e.g. 5-50 mM sodium phosphate, 20-200 mM sodium chloride pH 6-8; or a phosphate buffer or a citrate buffer or an acetate buffer or a mixture of these buffers with a total molarity of 1-100 mM, preferably 5-50 mM with 0-750 mM sodium chloride, pH 5-6.5; or affinity chromatography wash buffers described in the art.

Elution of TNFR2:Fc from the affinity matrix is preferably carried out by applying acidic conditions such as a pH ranging from 2.5 to 4.5, more preferably by applying a pH ranging from 3.0 to 3.5. In certain cases, it is desirable to apply a gradient starting from the higher pH towards the lower pH value. Elution may, for example, be carried out using a buffer comprising a buffer based on acetic acid, citric acid and/or phosphoric acid at concentrations of 1-100 mM, preferably 5-50 mM.

Additional parameters, such as flow rate, bed height of the column, etc. will have to be determined on a case by case basis using routine methods. However, to that end, it will be appreciated that affinity chromatographic procedures are well known in the art.

In a preferred embodiment, the at least one chromatographic step further comprises one or more ion exchange chromatography steps, which are preferably conducted prior to the HIC step.

For example, a cation exchange step may be applied. In particular if a method contains two ion exchange chromatographic steps, it is general practice to apply at least one cation exchange chromatographic step.

In a more preferred embodiment, the TNFR2:Fc is subjected to one or more steps of anion exchange chromatography following the affinity chromatography, which allows separation and purification of molecules based on their charge. The anion exchange chromatography may also use a multimodal chromatography (MMC) matrix, such as commercially available from GE Healthcare under the tradename Capto adhere. The anion exchange chromatography may be carried out in bind/elute mode or flow-through mode or both. In certain instances, it can be preferred that the anion exchange chromatography is first carried out in bind/elute mode followed by a second anion exchange step carried out in flow-through mode.

Merely as an example, in the following a classical anion exchange chromatography step in bind/elute mode is described.

The TNFR2:Fc is bound to the anion exchange resin at pH 7-8, preferably at pH 7.3-7.7. Once the TNFR2:Fc is bound to the anion exchange resin, said resin is washed with a buffer at pH 7-8, an appropriate washing buffer may be a phosphate buffer, e.g., a buffer comprising 1-50 mM sodium phosphate. Elution can be accomplished by using a buffer, such as a phosphate, citrate, or acetate buffer, or a mixture thereof, e.g. comprising 1-50 mM sodium phosphate, having a salt concentration that disturbs the ionic interaction between the TNFR:Fc and the anion exchange resin, for example, 100-200 mM sodium chloride.

Merely as an example, in the following a multimodal anion exchange chromatography step in flow-through mode is described.

For best results, conductivity of the TNFR2:Fc containing solution is adjusted to 20-60 mS/cm, preferably to 25-46 mS/cm; and to pH 5.5-6.5, preferably to pH 5.5-6.2. The buffer may be a phosphate, citrate, or acetate buffer, or a mixture thereof, e.g. a buffer comprising 1-50 mM sodium phosphate, sodium citrate or sodium acetate; and 200-700 mM sodium chloride, preferably 250-600 mM sodium chloride.

The fraction(s) obtained after the anion exchange chromatography step(s) comprising the TNFR:Fc could then be subjected to a hydrophobic interaction chromatography (HIC).

As set out above, the purification method comprises at least one step of hydrophobic interaction chromatography (HIC). At high salt concentrations, nonpolar groups on the protein surface interact with the hydrophobic groups, e.g. octyl or phenyl groups, of the HIC resin. Particular useful HIC resins are the commercially available Phenyl Sepharose HP (GE Healthcare) and Toyopearl Phenyl 650, e.g. Toyopearl Phenyl 650 (M). Since hydrophobic effects are augmented by increased ionic strength, the eluant is typically an aqueous buffer with decreasing salt concentrations, increasing concentrations of detergent (which disrupts hydrophobic interactions), and/or changes in pH. In a preferred embodiment, HIC is carried out in a buffer having a pH ranging from 5.5-6.5, preferably pH 5.8-6.5, such as a pH of 6.0.

Further, prior to binding of the TNFR2:Fc to the HIC resin, it may be necessary to adjust the fraction(s) comprising the TNFR2:Fc, so that the conductivity of the solution is in the range of 50-100 mS/cm, preferably 70-85 mS/cm. This may be achieved, for example, by diluting the fraction(s) comprising the TNFR2:Fc with a sodium citrate, sodium phosphate or sodium acetate buffer further comprising sodium sulphate at concentrations of or above 1M sodium sulphate.

After loading of the TNFR2:Fc, the HIC resin is washed with a suitable buffer. For example, the resin may be washed with a washing buffer comprising 50-150 mM sodium citrate, sodium phosphate or sodium acetate, preferably 50-100 mM sodium citrate or sodium phosphate; and an appropriate concentration of sodium sulphate. In a preferred embodiment, the resin is washed with a washing buffer comprising 100 mM sodium phosphate and 0.6M sodium sulphate; 50 mM sodium phosphate and 0.8M sodium sulphate; 50 mM sodium phosphate and 0.95M sodium sulphate; or 50 mM sodium citrate and 0.8M sodium sulphate. The concentration of the buffer and/or of the sodium sulphate may be chosen as a gradient, or may be each a single concentration falling within the above ranges.

In case elution is to be achieved by decreasing the salt concentration, the TNFR2:Fc can be eluted by applying a 0-100% gradient from said washing buffer to an elution buffer having a lower concentration of ions. For example, the elution buffer may be a citrate, phosphate or acetate buffer, preferably the same buffer system used in said washing buffer. More preferably, the elution buffer comprises 1-100 mM sodium citrate, sodium phosphate or sodium acetate, preferably 10-50 mM sodium citrate or sodium phosphate; and 0-100 mM sodium sulphate, and more preferably 0-10 mM sodium sulphate. Based on the actual data regarding yield and bioactivity for the eluted fractions obtained, the skilled person may select an optimal elution window, which represents the best compromise of yield, purity and bioactivity.

With the use of a HIC step, the degree of purity of the sample, as determined by size exclusion chromatography (SEC) can be increased to values above 90%, preferably above 92%, even more preferably above 95%. In particular, this HIC step allows for the reduction of product-related impurities, such as degradation products (DPs) of TNFR2:Fc, aggregation products (APs) of TNFR2:Fc, wrongly processed TNFR:Fc proteins or dimers, wrongly folded TNFR:Fc proteins or TNFR:Fc proteins or dimers with wrong intrachain and/or interchain disulphide bridging. It is understood by the skilled person that wrong disulphide bridging and wrong folding might be mutually dependent and/or synergistic. Specifically, the HIC step can be used to reduce the amount of $Cys_{78}$-$Cys_{88}$ disulphide bridged TNFR2:Fc.

In further preferred embodiments, the method may further comprise a step, wherein the eluate of the HIC step is subjected to nanofiltration, ultrafiltration and/or diafiltration, in order to separate any inactivated viruses or other contaminants from the purified solution and/or transfer the purified TNFR2:Fc into a more suitable buffer in order to render the TNFR2:Fc ready for further processing. For example, the purified TNFR2:Fc may be formulated into a pharmaceutical composition.

However, the percentage of $Cys_{78}$-$Cys_{88}$ disulphide bridged TNFR2:Fc is also dependent on the conditions during production (i.e. fermentation) of the TNFR2:Fc. Therefore, also provided is a method comprising
(a) producing a composition comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc in a suitable host cell; and
(b) purifying the obtained combination of $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc by the purification method as described above.

In a preferred embodiment, the TNFR2:Fc is produced using a CHO host cell. The TNFR2:Fc producing CHO cell culture production process is based on four phases:
1. Inoculation phase: After thawing of a cell bank vial the culture is expanded in a series of shake flasks of growing size to generate enough cell suspension to start the first bioreactor.
2. Expansion phase: After the inoculum train one or more bioreactor pre stage cultures are run to further expand the culture before starting production in the final bioreactor. The key parameter 'pH' is set-point controlled during this expansion phase. During both, inoculum and expansion phases, the culture is kept in the exponential growth phase by adequately controlling transfer and seeding cell densities.
3. Production phase: A batch, fed-batch, or perfusion cell culture production process is applied. If the original cell culture temperature is higher, e.g. 37° C., the temperature can be reduced during the production stage, e.g. to 30.5-36.5° C., preferably to 30.5-35° C., more preferably to a temperature of 31-34° C., even more preferably to a temperature of 31.5-33° C., and most preferably at a temperature of 31.5-32.5° C. However, it is equally feasible to keep the temperature constantly in the above ranges already from the beginning of the production range.
4. Clarification: After the end of the production phase, harvest is initiated. The cells are separated by centrifugation followed by filtration to remove debris.

The TNFR2:Fc producing CHO process can be run with the same or different media for the inoculation, expansion and production phases. Suitable media for glycoprotein production in CHO cells are known in the art and are disclosed e.g. in U.S. Pat. No. 6,048,728, WO 2011/134920 and WO 2011/134921. Preferably, all media and, if employed, any feeds are chemically defined and free of animal components.

As explained above, pH and temperature are critical parameters in avoiding the formation of $Cys_{78}$-$Cys_{88}$ disulphide bridged TNFR2:Fc.

Hence, in a preferred embodiment, the host cell in step (a) is cultured at a temperature of 30.5-36.5° C. during the production phase; preferably at a temperature of 30.5-35° C., more preferably at a temperature of 31-34° C., even more preferably at a temperature of 31.5-33° C., and most preferably at a temperature of 31.5-32.5° C. Moreover, said host cell is preferably cultured at a pH of 6.75-7.00 during the production phase; preferably at a pH of 6.80-6.95, and most preferably at a pH of 6.85-6.90. E.g., the pH can be controlled via pCO2 and/or a 2% NaOH solution. In this context, see also the data in the Examples section.

The composition of TNFR2:Fc, which can be obtained using the above methods disclosed herein, is particularly low in $Cys_{78}$-$Cys_{88}$ disulphide bridged TNFR2:Fc on the basis of total TNFR2:Fc. Therefore, the present disclosure also provides a composition of TNFR2:Fc, wherein the amino acid sequence of the TNFR2:Fc has at least 97%, preferably at least 98%, more preferably at least 99% identity; most preferably 100% to the amino acid sequence of SEQ ID NO: 3, comprising less than 2.2% $Cys_{78}$-$Cys_{88}$ disulphide bridged TNFR2:Fc, preferably less than 2.1%, preferably less than 2.0%, preferably less than 1.9%, preferably less than 1.8%, more preferably less than 1.7%, even more preferably less than 1.6%, and most preferably 1.5% or less $Cys_{78}$-$Cys_{88}$ disulphide bridged TNFR2:Fc, determined according to the method using peak integration of T7 and T27 as described above.

Such a composition may be used in medicine such as in a method of treating a subject, wherein the composition is administered to the subject. More specifically, the composition as disclosed herein may be used in the prevention and/or treatment of a disease selected from autoimmune disease, ankylosing spondylitis, juvenile rheumatoid arthritis, psoriasis, psoriatic arthritis, rheumatoid arthritis, granulomatosis, inflammatory bowel disease, chronic obstructive pulmonary disease (COPD), Hepatitis C, endometriosis, asthma, cachexia, atopic dermatitis, Alzheimer, and cancer; preferably in the treatment of a disease selected from ankylosing spondylitis, juvenile rheumatoid arthritis, psoriasis, psoriatic arthritis and rheumatoid arthritis.

The invention is further described by the following embodiments.
1. A method for determining $Cys_{78}$-$Cys_{88}$ disulphide bridged TNFR2:Fc in a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc, wherein the method comprises the steps of:

17

(a) providing a sample comprising a mixture of $Cys_{78}$-$Cys_{88}$ disulphide bridged TNFR2:Fc and $Cys_{74}$-$Cys_{88}$/$Cys_{78}$-$Cys_{96}$ disulphide bridged TNFR2:Fc;
(b) denaturing and alkylating the sample of step (a);
(c) subjecting the sample resulting from step (b) to tryptic digestion;
(d) subjecting the sample resulting from step (c) to HPLC, thereby separating fragments indicative of $Cys_{78}$-$Cys_{88}$ disulphide bridged TNFR2:Fc; and
(e) conducting a peak integration for the peak indicative of $Cys_{78}$-$Cys_{88}$ disulphide bridged TNFR2:Fc and for a peak not affected by disulphide bridging of $Cys_{74}$, $Cys_{78}$, $Cys_{88}$ and $Cys_{96}$, as obtained from step (d);
wherein the amino acid sequence of the TNFR2 part of TNFR2:Fc has at least 97%, preferably at least 98%, more preferably at least 99% identity; most preferably 100% identity to the amino acids 23-257 of the amino acid sequence of SEQ ID NO: 1.

2. The method of embodiment 1, wherein the amino acid sequence of the TNFR2:Fc applied to step (a) has at least 97%, preferably at least 98%, more preferably at least 99% identity; most preferably 100% to the amino acid sequence of SEQ ID NO: 3 (etanercept).

3. The method of embodiment 1 or 2, wherein the peak not affected by disulphide bridging of $Cys_{74}$, $Cys_{78}$, $Cys_{88}$ and $Cys_{96}$ is not affected by disulphide bridging at all and indicative of the total TNFR:Fc in the sample.

4. The method of embodiment 3, wherein the fragments indicative of $Cys_{78}$-$Cys_{88}$ disulphide bridged TNFR2:Fc comprise, preferably consist of the amino acid sequence shown in SEQ ID NO: 4 ("T7"); and wherein the fragments indicative of total TNFR2:Fc comprise, preferably consist of the amino acid sequence shown in SEQ ID NO: 5 ("T27").

5. The method of embodiment 4, wherein the relative amount of $Cys_{78}$-$Cys_{88}$ disulphide bridged TNFR2:Fc is determined by
(i) integrating the peak areas in the HPLC chromatogram indicative of $Cys_{78}$-$Cys_{88}$ disulphide bridged TNFR2:Fc ("T7 area") and indicative of total TNFR2:Fc ("T27 area"); and
(ii) calculating the relative amount according to formula (1).

$$rel.\ \%(T7) = \frac{area(T7)}{area(T7) + area(T27)} \times 100 \qquad (1)$$

6. The method of any one of the preceding embodiments, wherein step (b) is carried out in a buffer comprising 0.5-1.5M iodoacetamide, preferably 0.9-1.2M iodoacetamide.

7. The method of any one of the preceding embodiments, wherein step (b) is carried out in a buffer comprising 0.02%-0.5% of a cleavable surfactant, preferably 0.1%-0.2%; in particular wherein the surfactant is selected from sodium 3-[(2-methyl-2-undecyl-1,3-dioxolan-4-yl)methoxy]-1-propanesulfonate, sodium 3-((1-(furan-2-yl)undecyloxy)carbonylamino)propane-1-sulfonate, and sodium 3-(4-(1,1-bis(hexyloxy)ethyl)pyridinium-1-yl)propane-1-sulfonate; more preferably wherein the surfactant is sodium 3-[(2-methyl-2-undecyl-1,3-dioxolan-4-yl)methoxy]-1-propanesulfonate.

8. The method of any one of the preceding embodiments, wherein step (b) is carried out in a buffer having a pH in the range of 7 to 9, preferably 7.5 to 8.5, most preferably about pH 8.

18

9. The method of any one of the preceding embodiments, wherein step (b) is carried out in a TRIS buffer, preferably in a buffer comprising 10-100 mM TRIS, more preferably 20-80 mM TRIS.

10. The method of any one of the preceding embodiments, wherein step (b) is carried out at 40 to 70° C. for 30 to 60 min, preferably at 50 to 60° C. for 30 to 45 min.

11. The method of any one of the preceding embodiments, wherein step (c) comprises buffer exchanging the sample obtained from step (b) into a suitable digestion buffer.

12. The method of any one of the preceding embodiments, wherein step (c) is carried out in a digestion buffer having a pH in the range of 5 to 7, preferably 5.5 to 6.5.

13. The method of any one of the preceding embodiments, wherein step (c) is carried out in a digestion buffer comprising MES as the buffering agent, preferably in a buffer comprising 10-100 mM MES, more preferably 30-60 mM MES.

14. The method of any one of the preceding embodiments, wherein step (c) is carried out in a digestion buffer comprising 0.02%-0.5% of a cleavable surfactant, preferably 0.1%-0.2%; in particular wherein the surfactant is selected from sodium 3-[(2-methyl-2-undecyl-1,3-dioxolan-4-yl)methoxy]-1-propanesulfonate, sodium 3-((1-(furan-2-yl)undecyloxy)carbonylamino)propane-1-sulfonate, and sodium 3-(4-(1,1-bis(hexyloxy)ethyl)pyridinium-1-yl)propane-1-sulfonate; more preferably wherein the surfactant is sodium 3-[(2-methyl-2-undecyl-1,3-dioxolan-4-yl)methoxy]-1-propanesulfonate.

15. The method of any one of the preceding embodiments, wherein step (c) is carried out using an effective amount of trypsin for 1-24 h, preferably for 6-18 h; and at 32-38°, preferably at 36-37° C.

16. The method of any one of the preceding embodiments, wherein step (c) is terminated by addition of 1% formic acid in 10% acetonitrile.

17. The method of any one of the preceding embodiments, wherein step (d) is carried out in a mobile phase comprising 0.05%-0.5% TFA in water, preferably 0.1%-0.2% TFA in water.

18. A method of purifying $Cys_{74}$-$Cys_{88}$/$Cys_{78}$-$Cys_{96}$ disulphide bridged TNFR2:Fc, wherein the method comprises subjecting a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc to at least one chromatographic step, wherein the at least one chromatographic step comprises a hydrophobic interaction chromatography (HIC); and
separating one or more fractions comprising $Cys_{74}$-$Cys_{88}$/$Cys_{78}$-$Cys_{96}$ disulphide bridged TNFR2:Fc which have a reduced amount of $Cys_{78}$-$Cys_{88}$ disulphide bridged TNFR2:Fc as compared to the sample subjected to said at least one chromatographic step;
wherein said one or more fractions comprise less than 2.2% $Cys_{78}$-$Cys_{88}$ disulphide bridged TNFR2:Fc on the basis of total TNFR2:Fc, preferably less than 2.1%, preferably less than 2.0%, preferably less than 1.9%, preferably less than 1.8%, more preferably less than 1.7%, even more preferably less than 1.6%, and most preferably 1.5% or less $Cys_{78}$-$Cys_{88}$ disulphide bridged TNFR2:Fc when determined using a method according to embodiment 5.

19. A method of purifying $Cys_{74}$-$Cys_{88}$/$Cys_{78}$-$Cys_{96}$ disulphide bridged TNFR2:Fc, wherein the method comprises subjecting a sample comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc to at least one chromatographic step, wherein the at least one chromatographic step comprises a hydrophobic interaction chromatography (HIC); and separating one or more fractions comprising $Cys_{74}$-$Cys_{88}$/$Cys_{78}$-$Cys_{96}$ disulphide bridged TNFR2:Fc which have a reduced amount of $Cys_{78}$-$Cys_{88}$ disulphide bridged TNFR2:Fc as compared to the sample subjected to said at least one chromatographic step;

wherein the amount of $Cys_{78}$-$Cys_{88}$ disulphide bridged TNFR2:Fc is determined using a method according to any one of embodiments 1-17.

20. The method of embodiment 18 or 19, wherein the at least one chromatographic step further comprises one or more ion exchange chromatography steps, which are preferably conducted prior to the HIC.

21. The method of embodiment 20, wherein the one or more ion exchange chromatography steps are one or more anion exchange chromatography step or steps.

22. The method of embodiment 21, wherein at least one of the one or more anion exchange chromatography steps comprise a multimodal anion exchange chromatography.

23. The method of any one of embodiments 18-22, wherein the method further comprises an affinity chromatographic step, preferably using protein A or protein G; said affinity chromatographic step being conducted prior to any other chromatographic step.

24. The method of any one of embodiments 18-23, wherein the amino acid sequence of the TNFR2:Fc has at least 97%, preferably at least 98%, more preferably at least 99% identity; most preferably 100% to the amino acid sequence of SEQ ID NO: 3.

25. A method comprising
(a) producing a composition comprising $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc in a suitable host cell; and
(b) purifying the obtained combination of $Cys_{74}$-$Cys_{88}$/$Cys_{78}$-$Cys_{96}$ disulphide bridged TNFR2:Fc and $Cys_{78}$-$Cys_{88}$ disulphide bridged TNFR2:Fc by the purification method of any one of embodiments 18-24.

26. The method of embodiment 25, wherein said host cell is cultured at a temperature of 30.5-36.5° C. during the production phase; preferably at a temperature of 30.5-35° C., more preferably at a temperature of 31-34° C., even more preferably at a temperature of 31.5-33° C., and most preferably at a temperature of 31.5-32.5° C.

27. The method of embodiment 25 or 26, wherein said host cell is cultured at a pH of 6.75-7.00 during the production phase; preferably at a pH of 6.80-6.95, and most preferably at a pH of 6.85-6.90.

28. The method of any one of embodiments 25-27, wherein said host cell is a CHO cell.

29. A composition of TNFR2:Fc, wherein the amino acid sequence of the TNFR2:Fc has at least 97%, preferably at least 98%, more preferably at least 99% identity; most preferably 100% to the amino acid sequence of SEQ ID NO: 3, comprising less than 2.2% $Cys_{78}$-$Cys_{88}$ disulphide bridged TNFR2:Fc on the basis of total TNFR2:Fc, preferably less than 2.1%, preferably less than 2.0%, preferably less than 1.9%, preferably less than 1.8%, more preferably less than 1.7%, even more preferably less than 1.6%, and most preferably 1.5% or less $Cys_{78}$-$Cys_{88}$ disulphide bridged TNFR2:Fc, determined according to the method as defined in embodiment 5.

30. Composition as defined in embodiment 29, for use in medicine.

31. Composition as defined in embodiment 30, for use in the prevention and/or treatment of a disease selected from autoimmune disease, ankylosing spondylitis, juvenile rheumatoid arthritis, psoriasis, psoriatic arthritis, rheumatoid arthritis, granulomatosis, inflammatory bowel disease, chronic obstructive pulmonary disease (COPD), Hepatitis C, endometriosis, asthma, cachexia, atopic dermatitis, Alzheimer, and cancer; preferably in the treatment of a disease selected from ankylosing spondylitis, juvenile rheumatoid arthritis, psoriasis, psoriatic arthritis and rheumatoid arthritis.

32. The method of any one of embodiments 18-24, wherein the purification is performed in large scale (100 g of TNFR2:Fc or more).

In the following, the present invention is further illustrated by the following figures and examples, which are not intended to limit the scope of the present invention. All references cited herein are explicitly incorporated by reference.

DESCRIPTION OF THE SEQUENCES (human TNF receptor type 2; CD120b; p75/80; RefSeq (protein): NP_001057)
SEQ ID NO: 1
MAPVAVWAAL AVGLELWAAA HALPAQVAFT PYAPEPGSTC RLREYYDQTA QMCCSKCSPG   60

QHAKVFCTKT SDTVCDSCED STYTQLWNWV PECLSCGSRC SSDQVETQAC TREQNRICTC   120

```
RPGWYCALSK QEGCRLCAPL RKCRPGFGVA RPGTETSDVV CKPCAPGTFS NTTSSTDICR    180

PHQICNVVAI PGNASMDAVC TSTSPTRSMA PGAVHLPQPV STRSQHTQPT PEPSTAPSTS    240

FLLPMGPSPP AEGSTGDFAL PVGLIVGVTA LGLLIIGVVN CVIMTQVKKK PLCLQREAKV    300

PHLPADKARG TQGPEQQHLL ITAPSSSSSS LESSASALDR RAPTRNQPQA PGVEASGAGE    360

ARASTGSSDS SPGGHGTQVN VTCIVNVCSS SDHSSQCSSQ ASSTMGDTDS SPSESPKDEQ    420

VPFSKEECAF RSQLETPETL LGSTEEKPLP LGVPDAGMKP S                        461

(human IgG1 class heavy chain constant domain)
                                                           SEQ ID NO: 2
Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys (Etanercept)
                                                           SEQ ID NO: 3
LPAQVAFTPY APEPGSTCRL REYYDQTAQM CCSKCSPGQH AKVFCTKTSD TVCDSCEDST     60

YTQLWNWVPE CLSCGSRCSS DQVETQACTR EQNRICTCRP GWYCALSKQE GCRLCAPLRK    120

CRPGFGVARP GTETSDVVCK PCAPGTFSNT TSSTDICRPH QICNVVAIPG NASMDAVCTS    180

TSPTRSMAPG AVHLPQPVST RSQHTQPTPE PSTAPSTSFL LPMGPSPPAE GSTGDEPKSC    240

DKTHTCPPCP APELLGGPSV FLFPPKPKDT LMISRTPEVT CVVVDVSHED PEVKFNWYVD    300

GVEVHNAKTK PREEQYNSTY RVVSVLTVLH QDWLNGKEYK CKVSNKALPA PIEKTISKAK    360

GQPREPQVYT LPPSREEMTK NQVSLTCLVK GFYPSDIAVE WESNGQPENN YKTTPPVLDS    420

DGSFFLYSKL TVDKSRWQQG NVFSCSVMHE ALHNHYTQKS LSLSPGK                  467
```

EXAMPLES

Example 1

Determination of Relative Amount of T7

Figure 1:
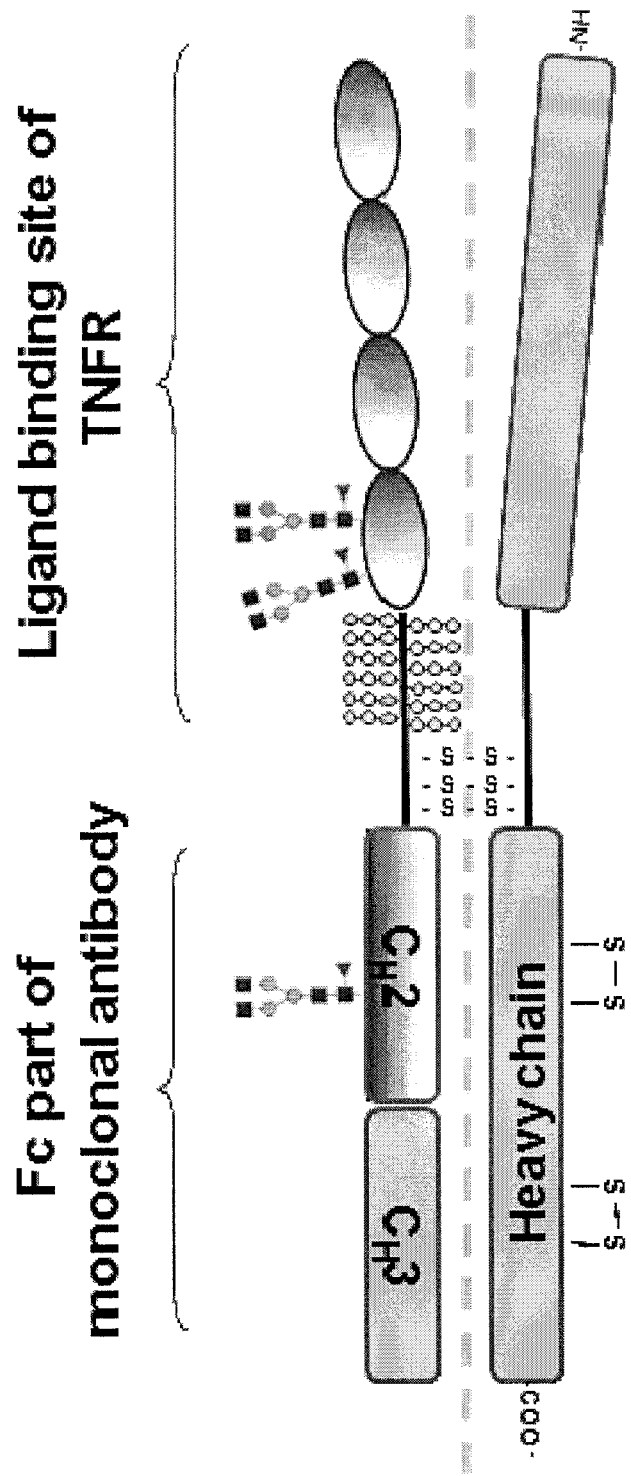
FIG. 1: Schematic illustration of TNFR2:Fc.
Figure 2:
FIG. 2: TNFR2:Fc (left), TNF-alpha (right).
Figure 3:
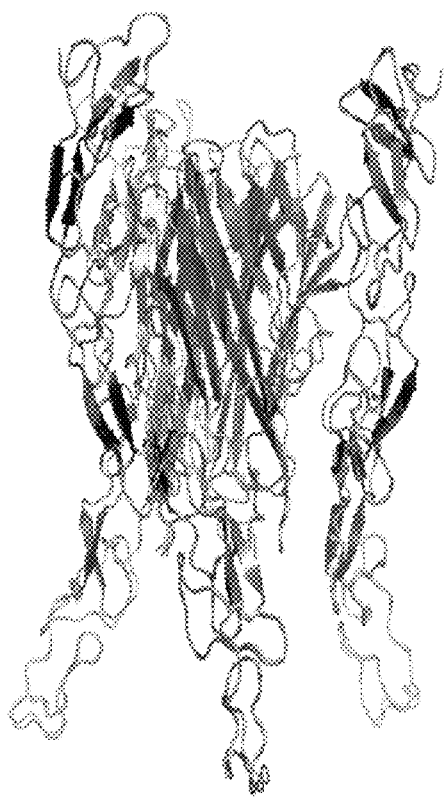
FIG. 3: Complex of TNFR2:Fc and TNF-alpha.
Figure 4:
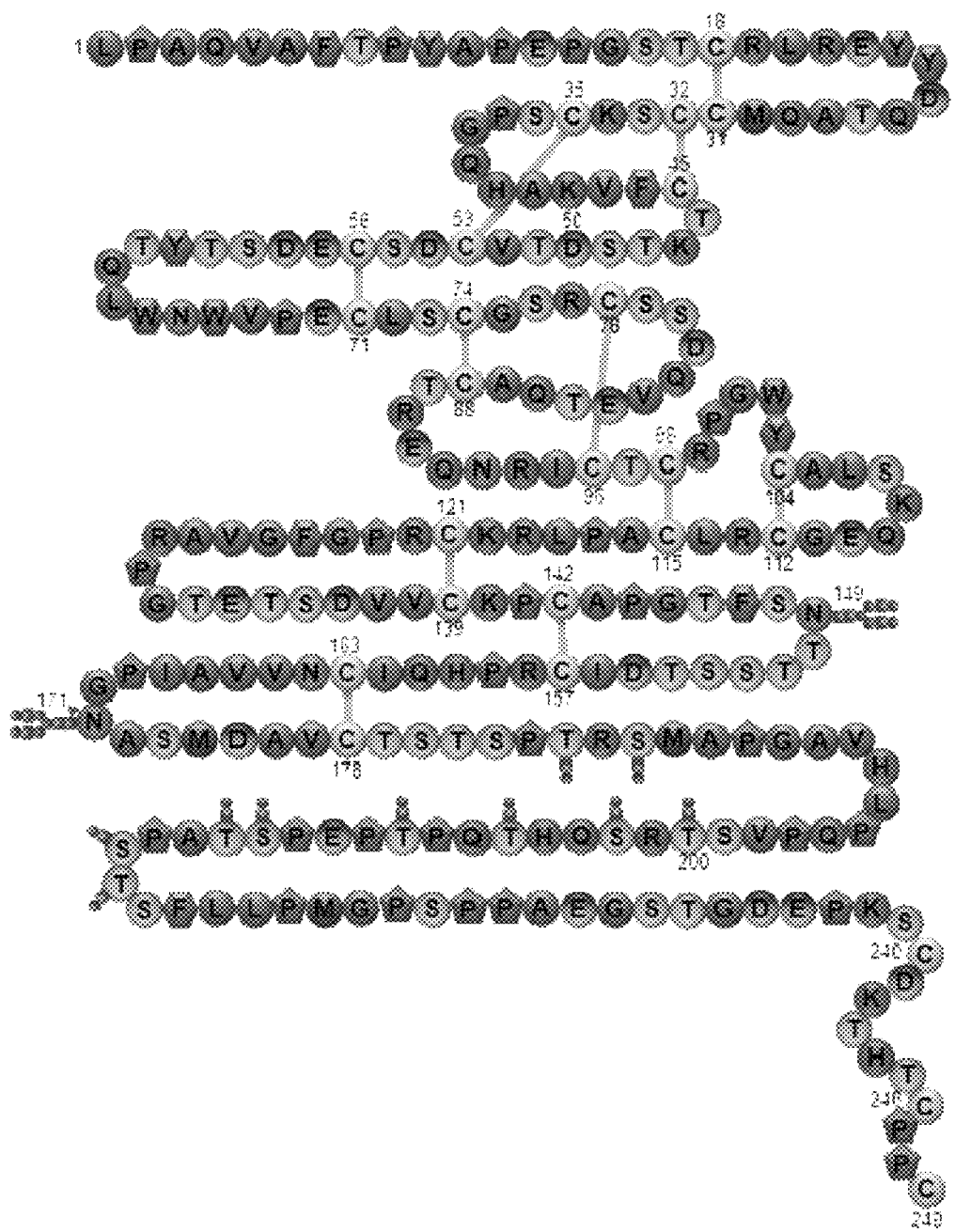
FIG. 4: Structural representation of the TNFR2:Fc N-terminal TNF alpha receptor domain (see also SEQ ID NO: 1). Amino acids are indicated by single letter code. Asparagine linked N-glycans and serine or threonine linked O-glycans are indicated graphically. Correct disulphide bridging is shown by light grey bars between specific cysteine residues.
Figure 6:
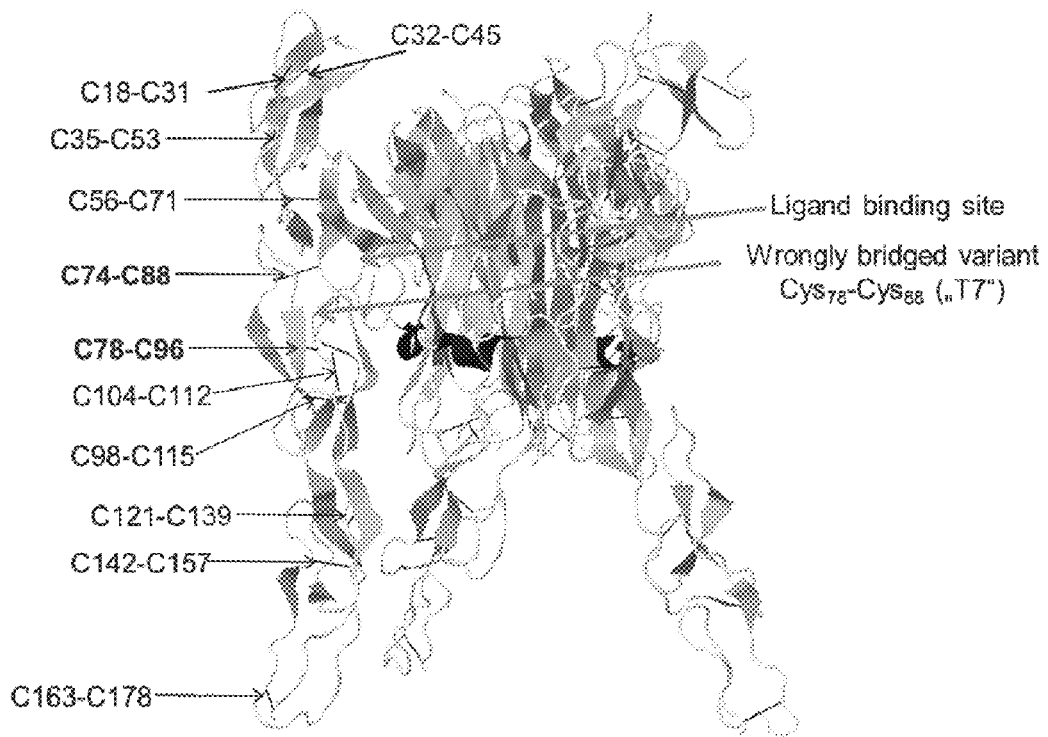
FIG. 6: Disulphide bridges of the receptor (X-ray structure taken from "Solution of the Structure of the TNF-TNFR2 Complex." Mukai et al., Sci Signal 3(148), ra83, November 2010; labeling of bridges and text added).

TNFR2:Fc is a fusion protein composed of a C-terminal Fc antibody domain and an N-terminal TNF alpha receptor 2 domain. The structure of the TNF alpha receptor domain 2 is critical for bioactivity of this biopharmaceutical and is highly complex containing multiple O-glycans, two N-glycans and eleven disulphide bridges (see FIGS. 4 and 6). It could be shown that at least one variant form of the molecule exists in the final TNFR2:Fc drug substance as a result of different disulphide bridging.

Figure 5:
FIG. 5: Structural representation of incorrectly disulphide bridged peptide T7 (see also SEQ ID NO: 4) and the internal reference peptide T27 (see also SEQ ID NO: 5). Amino acids are indicated by single letter code. The T7 peptide exhibits an aberrant disulphide bridge between cysteins 78 and 88 and its abundance correlates negatively with bioactivity. The reference peptide T27 is not involved in disulphide bridging.
Figure 5:
Figure 7:
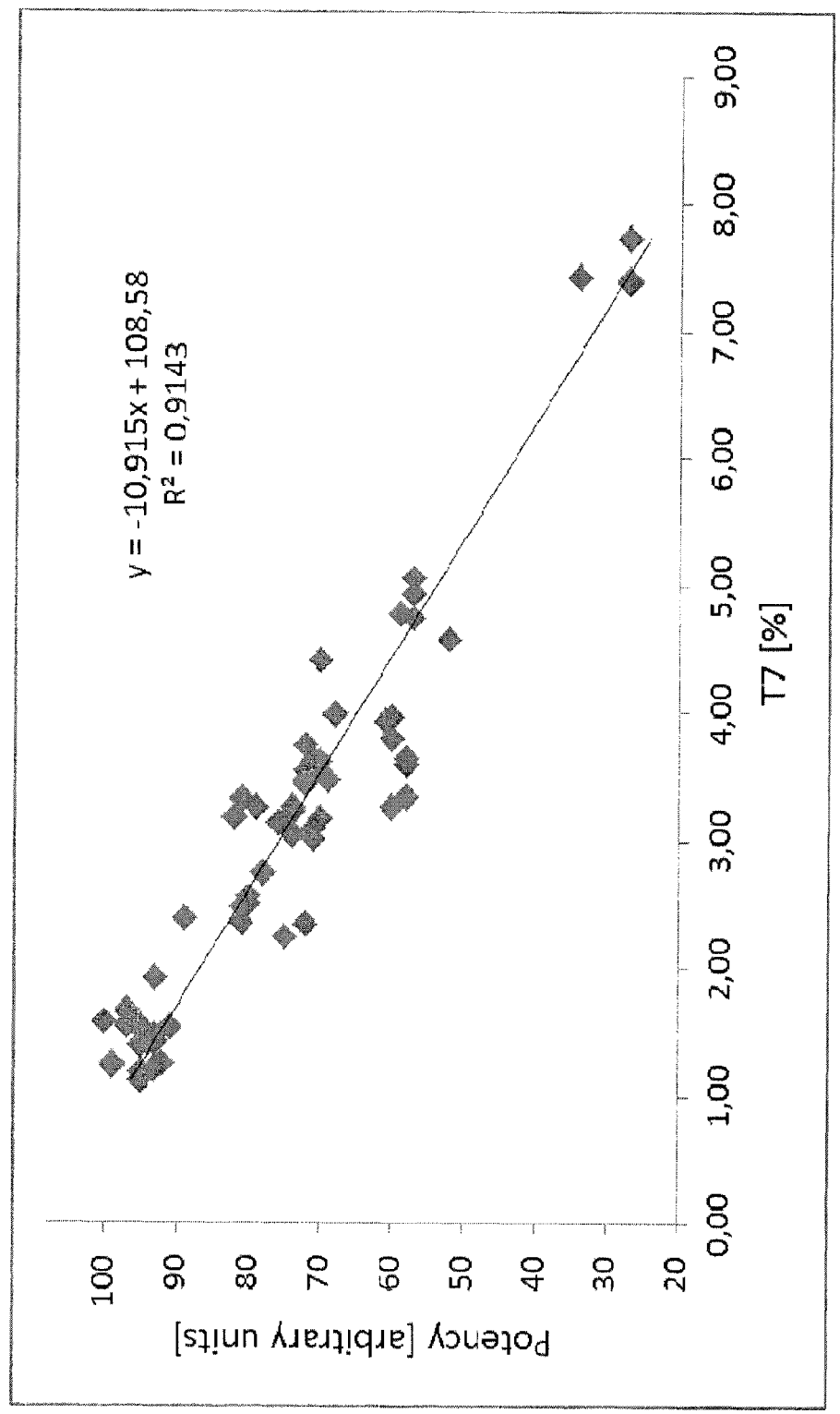
FIG. 7: Representative data showing the relative amount of T7 determined according to the method using peak integration of T7 and T27 as described above in different samples with varying levels of bioactivity. The potency on the y-axis was determined using a reporter gene assay, the values are arbitrary values. Samples of different quality were analyzed and the correlation was determined based on all data points shown.

By digesting TNFR2:Fc samples with trypsin under non-reducing conditions, the protein can be cleaved into smaller components, while the disulphide bridge structures remain intact. Elucidation of the peptides using RP-HPLC-MS analysis verified the presence of the expected correctly bridged peptides as well as a peptide termed T7, which was shown to contain an aberrant disulphide bridge between cysteins 78 and 88 (see FIGS. 5 and 6, and Table 2 above). While the abundance of some correctly bridged structures were found to correlate with increased bioactivity, their diversity and complex elution profiles precluded them from use as stable indicators of bioactivity using an LC-UV/Vis approach. However, the incorrectly bridged peptide T7 exhibited a stable correlation with reduced bioactivity. Representative data is shown in FIG. 7, demonstrating the strong correlation between bioactivity and the relative amount of T7 determined according to the method using peak integration of T7 and T27 as described above.

The relative T7 amount can be determined as follows.

All samples are thawed at room temperature. All centrifugation steps are carried out on a refrigerated centrifuge (e.g., Eppendorf Centrifuge 5804R; Eppendorf, Hamburg, Germany). About 80-300 µg, preferably 100-200 µg of protein are typically used per sample. In order to adapt the buffer it may be necessary to concentrate the samples to an appropriate protein concentration, e.g. by using a concentration device such as Vivaspin 500, Sartorius Art. Nr.: VS0102. To the samples or their concentrates, wash buffer (50 mM TRIS pH 8) is added to a final volume of about 200 µl of wash buffer. 100 µl of denaturation solution are added. The denaturation solution is prepared by mixing 950 µl of 0.1% RapiGest (Waters, no. 186001861) in 50 mM TRIS pH 8 with 50 µl M iodoacetamide (Sigma, no. 11149) in 50 mM TRIS pH 8. The reagent is prepared directly before use, and covered e.g. with aluminum foil for protection against light. Bubbles are removed by light tapping and the sample is incubated for 40 min at 50° C. (e.g. by using Thermomixer Comfort; Eppendorf Hamburg, Germany).

The samples are allowed to cool to room temperature and then buffer exchanged to a final volume of 20-40 µl of digestion buffer (50 mM MES (Sigma, M5287) in HPLC water pH 6). Then the samples are each transferred into a safe lock reaction tube, and 25 µl of 50 mM digestion buffer (50 mM MES in HPLC water pH)+25 µl of digestion buffer with surfactant (0.1% RapiGest (Waters, no. 186001861) in 50 mM MES pH 6 buffer) are added. 12 µl of the freshly reconstituted 1 µg/µl trypsin are added (Promega, Trypsin Gold, Mass Spec Grade, reconstituted with 50 mM MES pH 6.0 buffer directly before use). The sample is carefully agitated by gentle flicking, then spinned down shortly, and incubated for 17 h at 37° C. in a heating block (e.g. Thermomixer Comfort; Eppendorf Hamburg, Germany).

Following incubation, the samples are removed from the thermomixer, and 49 µl of termination solution (1% formic acid (HPLC grade, e.g., ThermoScientific, no. 40967) in 10% acetonitrile (acetonitrile of HPLC grade ≥99.9%, e.g. Merck no. (1.00030.2500)) are added. It is gently mixed by lightly flicking. The samples are centrifuged for approx. 10 min at 16,000 g and 6° C. A slight opaque pellet may be barely visible after centrifugation. If the sample is still opaque following this first centriguation, the centrifugation is repeated. Then the supernatant is transferred into a 300 µl autosampler glass vial, water is added to an overall volume of approximately 236 µl, and the samples are placed in a cooled autosampler.

HPLC is carried out using a liquid chromatograph with a UV detector (e.g. 1200SL Series LC system with online degasser (G1322A), binary pump module (G1312), thermostatted autosampler (G1329A/G1330A), thermostatted column department (G1316A), VWD detector (G1314A); all Agilent Technologies, Waldbronn, Germany) and a suitable column (e.g., Ascentis Express Peptide ES-C18, 2.1 mm ID×15 cm L Cat. No. 53307-U; Supelco). The following parameters are used:

| | |
|---|---|
| Run time: | 45 min |
| Flow rate: | 0.8 mL/min |
| CompressibilityLeftPump | 46 |
| CompressibilityRightPump | 115 |
| Column temperature: | 60° C. (=setpoint) |
| Injection volume: | 50 µL |
| Autosampler temperature: | 2-10° C. |
| UV detector: | Wavelength: 215 nm |
| | PeakWidth: 0.025 min |
| MWD/DAD detector: | Wavelength: 215 nm |
| | PeakWidth: 0.03 min |
| | Bandwidth: 4 nm |
| | No Reference |
| | SlitWidth: 4 nm |
| Mobile phase A | 0.1% TFA (HPLC grade, Fluka no. 40967) in HPLC water |
| Mobile phase B | 0.1% TFA in 90% Acetonitrile and 10% HPLC water |
| Gradient | |

TABLE 3

Gradient

| Time [min] | % B | Flow Rate [ml/min] |
|---|---|---|
| 0.0 | 0 | 0.8 |
| 2.5 | 0 | 0.8 |
| 25 | 16 | 0.8 |
| 28 | 18 | 0.8 |
| 33 | 100 | 0.8 |
| 37 | 100 | 0.8 |
| 40 | 0 | 0.8 |
| 45 | 0 | 0.8 |

To check for carryover, blank samples (mobile phase A) can be injected every e.g. 10th injection.

Integration of the chromatograms is performed using a suitable chromatography data system, e.g. Chromeleon (Dionex, Sunnyvale, Calif., USA). The relative amount of T7 peptide is calculated according to the following equation (formula (1)):

$$rel.\ \%(T7) = \frac{\text{area}(T7)}{\text{area}(T7) + \text{area}(T27)} \times 100 \tag{1}$$

Area(T7): peak area of T7
Area(T27): peak area of T27

To guarantee that proper amount of sample was applied onto the column, the peak area T27 in a given samples is compared to the average peak area of a reference substance injection. Calculations are performed according to following equation:

$$\text{Applied sample amount } [\%] = \frac{a_{sample}}{a_{reference}} * 100$$

$a_{sample}$ T27 peak area of TNFR:Fc sample
$a_{reference}$ average T27 peak area of TNFR:Fc reference substance injections All used substances were Ph. Eur. Grade or of comparable quality. The buffers were prepared with purified and deionized water. The suppliers and order numbers for instruments, materials and reagents indicated are given as examples. These products can be considered interchangeable with comparable products of the same or better quality.

Most notably, the relative amounts of T7 found in all US and EU batches of Enbrel® examined showed values of 2.3% or higher when analysed and calculated according to the determination method of the present invention using the T27 peptide's signal as reference peak, cf. Table 5.

TABLE 4

Relative amounts of T7 in the reference product Enbrel ®

| Batch | T7 [%] |
|---|---|
| #1026663 (US) | 2.4 |
| #F36988 (EU) | 2.4 |
| #F76195 (EU) | 2.8 |
| #1028435 (US) | 2.3 |
| #1026662 (US) | 2.3 |
| #F69006 (EU) | 2.8 |

This demonstrated that the methods of production and purification presented herein are capable of producing TNFR2:Fc and in particular etanercept at an unprecedented level of reduced T7 amount.

Example 2

Producing TNFR2:Fc with Varying Amounts of T7

It is known that wrongly bridged variants can already be formed in the upstream process (USP) for the manufacturing of TNFR2:Fc. By analyzing samples of DoE (Design of Experiments) process characterization studies it could be shown that the amount of wrongly bridged variants can be influenced on the USP level (see Table 4). The provided values are obtained from a statistical model. The TNFR2:Fc samples taken to establish this model were subjected only to Protein A affinity chromatography and not purified via hydrophobic interaction chromatography. The relative amount of T7 was determined according to the method using peak integration of T7 and T27 as described below.

TABLE 5

| pH | T7 [%] | 95% Confidence interval | | Temperature [° C.] | T7 [%] | 95% Confidence interval | |
|---|---|---|---|---|---|---|---|
| | | low limit | high limit | | | low limit | high limit |
| 6.65 | 3.86 | 3.59 | 4.14 | 30.5 | 2.21 | 1.92 | 2.5 |
| 6.70 | 3.59 | 3.42 | 3.76 | 31.5 | 2.4 | 2.24 | 2.55 |
| 6.80 | 3.25 | 3.12 | 3.38 | 33.0 | 3.19 | 3.05 | 3.32 |
| 6.90 | 3.2 | 3.04 | 3.35 | 34.5 | 4.59 | 4.3 | 4.88 |
| 6.95 | 3.27 | 3.07 | 3.48 | 35.5 | 5.87 | 5.31 | 6.42 |

Example 3

Purification of TNFR2:Fc

During downstream processing (DSP), wrongly bridged variants are mainly depleted on the HIC purification step, while small amounts may already be depleted by a previous anion exchange purification step, such as a MMC purification step in flow-through mode.

Affinity Chromatography (Protein A)

The purification process starts from cell free culture supernatants. The material was 0.2 μm filtered. Utilizing the Fc part of the fusion protein, TNFR:Fc was captured by affinity chromatography on Protein A resin. The Protein A interaction with the Fc part is very specific. Therefore, the capture chromatography very efficiently separates host cell proteins (HCPs), DNA and virus from the product.

Process temperature was 21° C. The cell culture supernatant was loaded onto MabSelect SuRe resin (GE Healthcare), equilibrated with sodium phosphate buffer of pH 7.0 further comprising 150 mM sodium chloride. Then, the column was washed with the same buffer until $UV_{280}$ returns to signal close to baseline (about 2 to 6 column volumes).

To increase the HCP removal capacity of the capture step, an additional wash step was introduced. This wash buffer contained sodium acetate and 0-500 mM sodium chloride. It was followed by product elution with an acidic buffer having a pH of ~3.2. The eluates were combined and processed to the next purification step.

Anion Exchange Chromatography (AEX)

The intermediate resulting from the affinity chromatography step was adjusted to pH 7.5 and loaded onto a Fractogel TMAE HiCap (M) resin (Merck). Subsequently, the column was rinsed with sodium phosphate buffer and finally the product was eluted with sodium phosphate buffer containing 150 mM sodium chloride. The eluates were combined and processed to the next purification step.

MM Chromatography (MMC)

The combined eluates from the anion exchange chromatography step were adjusted in conductivity using 4M sodium chloride, and the pH was adjusted to pH 6.0 using a phosphoric acid solution of pH ≤2. Then the intermediate was loaded onto Capto adhere resin (GE Healthcare), equilibrated with 20 mM sodium phosphate, 450 mM sodium chloride pH 6.0 and the column was then washed with 20 mM sodium phosphate, 450 mM sodium chloride pH 6.0. The flow through and the early wash comprising the product were collected and pooled.

Hydrophobic Interaction chromatography (HIC)

The pooled fractions from the MM chromatography were diluted with sodium citrate buffer pH 6.0 comprising 1.4M sodium sulfate. The conductivity of the solution was about 80 mS/cm. Then, the solution was loaded onto Toyopearl Phenyl 650 (M) and equilibrated with sodium citrate buffer pH 6.0 comprising sodium sulfate. The column is then rinsed with the same buffer. Finally, the column is eluted using a 0-100% gradient from the equilibration buffer to elution buffer (25 mM sodium citrate pH 6.0).

The purity of the product was determined using size exclusion chromatography (SEC), and by determining the amount of DNA, host cell proteins (HCP), Protein A, and endotoxin. Further, the step yield and total yield was calculated for each purification step. The following Table 8 shows data obtained with the above described method for at least three runs.

TABLE 6

Depletion of peptide T7 during downstream processing

| Batch | Purification steps | T7 [%] | Potency [arbitrary units] |
|---|---|---|---|
| 1 | Prot A | 3.63 | 71 |
| 1 | +AEX +MMC | 3.05 | 74 |

TABLE 6-continued

Depletion of peptide T7 during downstream processing

| Batch | Purification steps | T7 [%] | Potency [arbitrary units] |
|---|---|---|---|
| 1 | +HIC | 1.54 | 91 |
| 2 | Prot A | 3.44 | 72 |
| 2 | +AEX +MMC | 3.16 | 75 |
| 2 | +HIC | 1.23 | 93 |

Example 4

Stability Under Stress Conditions

Applying the methods disclosed herein allows obtaining TNFR:Fc preparations with a decreased relative T7 amount as compared to TNFR:Fc preparations in the state of the art.

The low amount of T7 is also maintained upon stress treatment.

TABLE 7

| Sample No. | | T7 relative to T27 (% T7) |
|---|---|---|
| 3 | Final formulation | 1.2 |
| 3 | 1 month @ 40° C. | 1.8 |
| 4 | 1 month @ 40° C. | 1.9 |

LIST OF REFERENCES

U.S. Pat. No. 7,294,481
U.S. Pat. No. 6,048,728
WO 2011/134920
WO 2011/134921
Mukai et al. (2010) "Solution of the Structure of the TNF-TNFR2 Complex.", Sci Signal 3 (148), ra83

The invention claimed is:

1. A method for determining a relative amount of $Cys_{78}$-$Cys_{88}$ disulfide bridged TNFR2:Fc in a sample comprising $Cys_{74}$-$Cys_{88}$/$Cys_{78}$-$Cys_{96}$ disulfide bridged TNFR2:Fc and $Cys_{78}$-$Cys_{88}$ disulfide bridged TNFR2:Fc, wherein the method comprises the steps of:

(a) providing a sample comprising a mixture of $Cys_{78}$-$Cys_{88}$ disulfide bridged TNFR2:Fc and $Cys_{74}$-$Cys_{88}$/$Cys_{78}$-$Cys_{96}$ disulfide bridged TNFR2:Fc;

(b) denaturing and alkylating the sample of step (a);

(c) subjecting the sample resulting from step (b) to tryptic digestion under non-reducing conditions;

(d) determining by HPLC the amount of a fragment indicative of $Cys_{78}$-$Cys_{88}$ disulfide bridged TNFR2:Fc in the sample resulting from step (c); and (e) determining the relative amount of the $Cys_{78}$-$Cys_{88}$ disulfide bridged TNFR2:Fc in the sample based on the amount of the fragment indicative of $Cys_{78}$-$Cys_{88}$ disulfide bridged TNFR2:Fc relative to the amount of a fragment not affected by disulfide bridging of $Cys_{74}$, $Cys_{78}$, $Cys_{88}$ and $Cys_{96}$;

wherein the amino acid sequence of the TNFR2 part of TNFR2:Fc has at least 97% identity to the amino acids 1-235 of the amino acid sequence of SEQ ID NO: 1, and wherein the fragment indicative of $Cys_{78}$-$Cys_{88}$ disulfide bridged TNFR2:Fc consists of SEQ ID NO:4 ("T7").

2. The method of claim 1, wherein the amino acid sequence of the TNFR2:Fc applied to step (a) has at least 97% identity to the amino acid sequence of SEQ ID NO: 3 ("etanercept").

3. The method of claim 1, wherein the peak not affected by disulfide bridging of $Cys_{74}$, $Cys_{78}$, $Cys_{88}$ and $Cys_{96}$ is not affected by disulfide bridging at all and is indicative of the total TNFR2:Fc in the sample.

4. The method of claim 3, wherein the fragment indicative of total TNFR2:Fc comprises the amino acid sequence shown in SEQ ID NO: 5 ("T27").

5. The method of claim 4, wherein the fragment indicative of total TNFR2:Fc consists of the amino acid sequence shown in SEQ ID NO: 5 ("T27").

6. The method of claim 4, wherein the relative amount of $Cys_{78}$-$Cys_{88}$ disulfide bridged TNFR2:Fc is determined by
   (i) determining the peak areas in the HPLC chromatogram indicative of $Cys_{78}$-$Cys_{88}$ disulfide bridged TNFR2:Fc ("T7 area") and indicative of total TNFR2:Fc ("T27 area"); and
   (ii) calculating the relative amount according to formula (1)

$$x(in\ \%) = \frac{[T7\ area]}{[T7\ area] + [T27\ area]} \times 100. \quad (1)$$

7. The method of claim 1, wherein step (b) is carried out in a buffer having a pH in the range of 7 to 9, and wherein the buffer comprises at least one of:
   10-100 mM TRIS,
   0.5-1.5 M iodoacetamide, and
   0.02%-0.5% of a cleavable surfactant.

8. The method of claim 7, wherein step (b) is carried out in a buffer having a pH in the range of 7.5 to 8.5, and wherein the buffer comprises at least one of:
   20-80 mM TRIS,
   0.9-1.2 M iodoacetamide, and
   0.1%-0.2% of a cleavable surfactant.

9. The method of claim 8, wherein the buffer comprises a cleavable surfactant which is selected from the group consisting of:
   sodium 3-[(2-methyl-2-undecyl-1,3-dioxolan-4-yl)methoxy]-1-propanesulfonate,
   sodium 3-((1-(furan-2-yl)undecyloxy)carbonylamino)propane-1-sulfonate, and
   sodium 3-(4-(1,1-bis(hexyloxy)ethyl)pyridinium-1-yl)propane-1-sulfonate.

10. The method of claim 9, wherein the cleavable surfactant is sodium 3-[(2-methyl-2-undecyl-1,3-dioxolan-4-yl)methoxy]-1-propanesulfonate.

11. The method of claim 1, wherein step (b) is carried out at 40 to 70° C. for 30 to 60 min.

12. The method of claim 1, wherein step (b) is carried out at 50 to 60° C. for 30 to 45 min.

13. The method of claim 1, wherein step (c) is carried out in a digestion buffer having a pH in the range of 5 to 7; and wherein the digestion buffer comprises:
   MES as the buffering agent; or
   0.02%-0.5% of a cleavable surfactant; or
   MES as the buffering agent and 0.02%-0.5% of a cleavable surfactant.

14. The method of claim 13, wherein step (c) is carried out in a digestion buffer having a pH in the range of 5.5 to 6.5; and wherein the digestion buffer comprises:
   10-100 mM MES as the buffering agent; or
   0.1%-0.2% of a cleavable surfactant; or
   10-100 mM MES as the buffering agent and 0.1%-0.2% of a cleavable surfactant.

15. The method of claim 13, wherein the buffer comprises a cleavable surfactant which is selected from the group consisting of:
   sodium 3-[(2-methyl-2-undecyl-1,3-dioxolan-4-yl)methoxy]-1-propanesulfonate,
   sodium 3-((1-(furan-2-yl)undecyloxy)carbonylamino)propane-1-sulfonate, and
   sodium 3-(4-(1,1-bis(hexyloxy)ethyl)pyridinium-1-yl)propane-1-sulfonate.

16. The method of claim 15, wherein the cleavable surfactant is sodium 3-[(2-methyl-2-undecyl-1,3-dioxolan-4-yl)methoxy]-1-propanesulfonate.

17. The method of claim 1, wherein step (c) is carried out using an effective amount of trypsin for 1-24 h; and at 32-38° C.

18. The method of claim 17, wherein step (c) is carried out using an effective amount of trypsin for 6-18 h; and at 36-37° C.

19. The method of claim 1, wherein step (d) is carried out in a mobile phase comprising 0.05%-0.5% TFA in water.

20. The method of claim 19, wherein step (d) is carried out in a mobile phase comprising 0.1%-0.2% TFA in water.

* * * * *

SEQUENCE LISTING

```
<160> NUMBER OF SEQ ID NOS: 36

<210> SEQ ID NO 1
<211> LENGTH: 461
<212> TYPE: PRT
<213> ORGANISM: homo sapiens

<400> SEQUENCE: 1

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
```

```
            225                 230                 235                 240
        Phe Leu Leu Pro Met Gly Pro Ser Pro Pro Ala Glu Gly Ser Thr Gly
                        245                 250                 255

Asp Phe Ala Leu Pro Val Gly Leu Ile Val Gly Val Thr Ala Leu Gly
                        260                 265                 270

Leu Leu Ile Ile Gly Val Val Asn Cys Val Ile Met Thr Gln Val Lys
                        275                 280                 285

Lys Lys Pro Leu Cys Leu Gln Arg Glu Ala Lys Val Pro His Leu Pro
                        290                 295                 300

Ala Asp Lys Ala Arg Gly Thr Gln Gly Pro Glu Gln Gln His Leu Leu
        305                 310                 315                 320

Ile Thr Ala Pro Ser Ser Ser Ser Ser Leu Glu Ser Ser Ala Ser
                        325                 330                 335

Ala Leu Asp Arg Arg Ala Pro Thr Arg Asn Gln Pro Gln Ala Pro Gly
                        340                 345                 350

Val Glu Ala Ser Gly Ala Gly Glu Ala Arg Ala Ser Thr Gly Ser Ser
                        355                 360                 365

Asp Ser Ser Pro Gly Gly His Gly Thr Gln Val Asn Val Thr Cys Ile
                        370                 375                 380

Val Asn Val Cys Ser Ser Ser Asp His Ser Ser Gln Cys Ser Ser Gln
        385                 390                 395                 400

Ala Ser Ser Thr Met Gly Asp Thr Asp Ser Ser Pro Ser Glu Ser Pro
                        405                 410                 415

Lys Asp Glu Gln Val Pro Phe Ser Lys Glu Glu Cys Ala Phe Arg Ser
                        420                 425                 430

Gln Leu Glu Thr Pro Glu Thr Leu Leu Gly Ser Thr Glu Glu Lys Pro
                        435                 440                 445

Leu Pro Leu Gly Val Pro Asp Ala Gly Met Lys Pro Ser
                        450                 455                 460

<210> SEQ ID NO 2
        <211> LENGTH: 330
        <212> TYPE: PRT
        <213> ORGANISM: Homo sapiens

<400> SEQUENCE: 2

Ala Ser Thr Lys Gly Pro Ser Val Phe Pro Leu Ala Pro Ser Ser Lys
        1               5                   10                  15

Ser Thr Ser Gly Gly Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Ser Leu Gly Thr Gln Thr
        65                  70                  75                  80

Tyr Ile Cys Asn Val Asn His Lys Pro Ser Asn Thr Lys Val Asp Lys
                        85                  90                  95

Lys Val Glu Pro Lys Ser Cys Asp Lys Thr His Thr Cys Pro Pro Cys
                        100                 105                 110

Pro Ala Pro Glu Leu Leu Gly Gly Pro Ser Val Phe Leu Phe Pro Pro
                        115                 120                 125

Lys Pro Lys Asp Thr Leu Met Ile Ser Arg Thr Pro Glu Val Thr Cys
                        130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 467
<212> TYPE: PRT
<213> ORGANISM: artificial
<220> FEATURE:
<223> OTHER INFORMATION: Etanercept

<400> SEQUENCE: 3

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175
```

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 4
<211> LENGTH: 13
<212> TYPE: PRT
<213> ORGANISM: Homo sapiens

<400> SEQUENCE: 4

Cys Ser Ser Asp Gln Val Glu Thr Gln Ala Cys Thr Arg
1               5                   10

<210> SEQ ID NO 5
<211> LENGTH: 8
<212> TYPE: PRT
<213> ORGANISM: Homo sapiens

<400> SEQUENCE: 5

Ala Leu Pro Ala Pro Ile Glu Lys
1               5

<210> SEQ ID NO 6
<211> LENGTH: 19
<212> TYPE: PRT
<213> ORGANISM: Homo sapiens

<400> SEQUENCE: 6

Leu Pro Ala Gln Val Ala Phe Thr Pro Tyr Ala Pro Glu Pro Gly Ser
1               5                   10                  15

Thr Cys Arg

<210> SEQ ID NO 7
<211> LENGTH: 13
<212> TYPE: PRT
<213> ORGANISM: Homo sapiens

<400> SEQUENCE: 7

Glu Tyr Tyr Asp Gln Thr Ala Gln Met Cys Cys Ser Lys
1               5                   10

<210> SEQ ID NO 8
<211> LENGTH: 8
<212> TYPE: PRT
<213> ORGANISM: Homo sapiens

<400> SEQUENCE: 8

Cys Ser Pro Gly Gln His Ala Lys
1               5

<210> SEQ ID NO 9
<211> LENGTH: 5
<212> TYPE: PRT
<213> ORGANISM: Homo sapiens

<400> SEQUENCE: 9

Val Phe Cys Thr Lys
1               5

<210> SEQ ID NO 10
<211> LENGTH: 30
<212> TYPE: PRT
<213> ORGANISM: Homo sapiens

<400> SEQUENCE: 10

Thr Ser Asp Thr Val Cys Asp Ser Cys Glu Asp Ser Thr Tyr Thr Gln
1               5                   10                  15

Leu Trp Asn Trp Val Pro Glu Cys Leu Ser Cys Gly Ser Arg
            20                  25                  30

<210> SEQ ID NO 11
<211> LENGTH: 4
<212> TYPE: PRT
<213> ORGANISM: Homo sapiens

<400> SEQUENCE: 11

Glu Gln Asn Arg
1

<210> SEQ ID NO 12
<211> LENGTH: 14
<212> TYPE: PRT
<213> ORGANISM: Homo sapiens

<400> SEQUENCE: 12

```
Ile Cys Thr Cys Arg Pro Gly Trp Tyr Cys Ala Leu Ser Lys
1               5                   10
```

<210> SEQ ID NO 13
<211> LENGTH: 5
<212> TYPE: PRT
<213> ORGANISM: Homo sapiens

<400> SEQUENCE: 13

```
Gln Glu Gly Cys Arg
1               5
```

<210> SEQ ID NO 14
<211> LENGTH: 6
<212> TYPE: PRT
<213> ORGANISM: Homo sapiens

<400> SEQUENCE: 14

```
Leu Cys Ala Pro Leu Arg
1               5
```

<210> SEQ ID NO 15
<211> LENGTH: 65
<212> TYPE: PRT
<213> ORGANISM: Homo sapiens

<400> SEQUENCE: 15

```
Cys Arg Pro Gly Phe Gly Val Ala Arg Pro Gly Thr Glu Thr Ser Asp
1               5                   10                  15

Val Val Cys Lys Pro Cys Ala Pro Gly Thr Phe Ser Asn Thr Thr Ser
            20                  25                  30

Ser Thr Asp Ile Cys Arg Pro His Gln Ile Cys Asn Val Val Ala Ile
                35                  40                  45

Pro Gly Asn Ala Ser Met Asp Ala Val Cys Thr Ser Thr Ser Pro Thr
            50                  55                  60

Arg
65
```

<210> SEQ ID NO 16
<211> LENGTH: 16
<212> TYPE: PRT
<213> ORGANISM: Homo sapiens

<400> SEQUENCE: 16

```
Ser Met Ala Pro Gly Ala Val His Leu Pro Gln Pro Val Ser Thr Arg
1               5                   10                  15
```

<210> SEQ ID NO 17
<211> LENGTH: 37
<212> TYPE: PRT
<213> ORGANISM: Homo sapiens

<400> SEQUENCE: 17

```
Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
            20                  25                  30

Gly Asp Glu Pro Lys
                35
```

<210> SEQ ID NO 18
<211> LENGTH: 4

```
<212> TYPE: PRT
<213> ORGANISM: Homo sapiens

<400> SEQUENCE: 18

Ser Cys Asp Lys
1

<210> SEQ ID NO 19
<211> LENGTH: 26
<212> TYPE: PRT
<213> ORGANISM: Homo sapiens

<400> SEQUENCE: 19

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25

<210> SEQ ID NO 20
<211> LENGTH: 7
<212> TYPE: PRT
<213> ORGANISM: Homo sapiens

<400> SEQUENCE: 20

Asp Thr Leu Met Ile Ser Arg
1               5

<210> SEQ ID NO 21
<211> LENGTH: 19
<212> TYPE: PRT
<213> ORGANISM: Homo sapiens

<400> SEQUENCE: 21

Thr Pro Glu Val Thr Cys Val Val Val Asp Val Ser His Glu Asp Pro
1               5                   10                  15

Glu Val Lys

<210> SEQ ID NO 22
<211> LENGTH: 14
<212> TYPE: PRT
<213> ORGANISM: Homo sapiens

<400> SEQUENCE: 22

Phe Asn Trp Tyr Val Asp Gly Val Glu Val His Asn Ala Lys
1               5                   10

<210> SEQ ID NO 23
<211> LENGTH: 4
<212> TYPE: PRT
<213> ORGANISM: Homo sapiens

<400> SEQUENCE: 23

Thr Lys Pro Arg
1

<210> SEQ ID NO 24
<211> LENGTH: 9
<212> TYPE: PRT
<213> ORGANISM: Homo sapiens

<400> SEQUENCE: 24

Glu Glu Gln Tyr Asn Ser Thr Tyr Arg
1               5
```

```
<210> SEQ ID NO 25
<211> LENGTH: 16
<212> TYPE: PRT
<213> ORGANISM: Homo sapiens

<400> SEQUENCE: 25

Val Val Ser Val Leu Thr Val Leu His Gln Asp Trp Leu Asn Gly Lys
1               5                   10                  15

<210> SEQ ID NO 26
<211> LENGTH: 4
<212> TYPE: PRT
<213> ORGANISM: Homo sapiens

<400> SEQUENCE: 26

Val Ser Asn Lys
1

<210> SEQ ID NO 27
<211> LENGTH: 4
<212> TYPE: PRT
<213> ORGANISM: Homo sapiens

<400> SEQUENCE: 27

Thr Ile Ser Lys
1

<210> SEQ ID NO 28
<211> LENGTH: 4
<212> TYPE: PRT
<213> ORGANISM: Homo sapiens

<400> SEQUENCE: 28

Gly Gln Pro Arg
1

<210> SEQ ID NO 29
<211> LENGTH: 11
<212> TYPE: PRT
<213> ORGANISM: Homo sapiens

<400> SEQUENCE: 29

Glu Pro Gln Val Tyr Thr Leu Pro Pro Ser Arg
1               5                   10

<210> SEQ ID NO 30
<211> LENGTH: 5
<212> TYPE: PRT
<213> ORGANISM: Homo sapiens

<400> SEQUENCE: 30

Glu Glu Met Thr Lys
1               5

<210> SEQ ID NO 31
<211> LENGTH: 10
<212> TYPE: PRT
<213> ORGANISM: Homo sapiens

<400> SEQUENCE: 31

Asn Gln Val Ser Leu Thr Cys Leu Val Lys
1               5                   10

<210> SEQ ID NO 32
```

```
<211> LENGTH: 22
<212> TYPE: PRT
<213> ORGANISM: Homo sapiens

<400> SEQUENCE: 32

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 33
<211> LENGTH: 17
<212> TYPE: PRT
<213> ORGANISM: Homo sapiens

<400> SEQUENCE: 33

Thr Thr Pro Pro Val Leu Asp Ser Asp Gly Ser Phe Phe Leu Tyr Ser
1               5                   10                  15

Lys

<210> SEQ ID NO 34
<211> LENGTH: 5
<212> TYPE: PRT
<213> ORGANISM: Homo sapiens

<400> SEQUENCE: 34

Leu Thr Val Asp Lys
1               5

<210> SEQ ID NO 35
<211> LENGTH: 23
<212> TYPE: PRT
<213> ORGANISM: Homo sapiens

<400> SEQUENCE: 35

Trp Gln Gln Gly Asn Val Phe Ser Cys Ser Val Met His Glu Ala Leu
1               5                   10                  15

His Asn His Tyr Thr Gln Lys
            20

<210> SEQ ID NO 36
<211> LENGTH: 8
<212> TYPE: PRT
<213> ORGANISM: Homo sapiens

<400> SEQUENCE: 36

Ser Leu Ser Leu Ser Pro Gly Lys
1               5
```